United States Patent [19]

Payne et al.

[11] Patent Number: 5,164,180
[45] Date of Patent: Nov. 17, 1992

[54] *BACILLUS THURINGIENSIS* ISOLATES ACTIVE AGAINST LEPIDOPTERAN PESTS

[75] Inventors: Jewel Payne, San Diego; August J. Sick, Oceanside, both of Calif.

[73] Assignee: Mycogen Corporation, San Diego, Calif.

[21] Appl. No.: 451,389

[22] Filed: Dec. 14, 1989

Related U.S. Application Data

[63] Continuation-in-part of Ser. No. 353,860, May 18, 1989, abandoned.

[51] Int. Cl.$^5$ .................... A01N 63/00; C12N 1/20
[52] U.S. Cl. ................... 424/93 L; 435/252.5; 435/832
[58] Field of Search ............... 424/93, 93 L; 435/712, 435/91, 170, 172.1, 172.3, 252.5, 252.3, 252.31, 252.33, 252.34, 254, 320.1, 832; 536/27; 935/6, 9, 22, 24, 27, 29, 33, 66, 68, 72, 73, 59, 60, 61

[56] References Cited

U.S. PATENT DOCUMENTS

| | | | |
|---|---|---|---|
| 4,448,885 | 5/1984 | Schnepf et al. | 435/252.3 |
| 4,467,036 | 8/1984 | Schnepf et al. | 435/320.1 |
| 4,713,241 | 12/1987 | Wakisaka et al. | 424/93 |

OTHER PUBLICATIONS

Shnepf, H. E. and H. R. Whiteley (1981) "Cloning and expression of the *Bacillus thringiensis* crystal protein gene in *Escherichia coli*," Proc. Natl. Acad. Sci. USA vol. 78 5:2893-2897.

*Primary Examiner*—Richard A. Schwartz
*Assistant Examiner*—John LeGuyader
*Attorney, Agent, or Firm*—Saliwanchik & Saliwanchik

[57] ABSTRACT

Novel *Bacillus thuringiensis* genes encoding toxins which are active against lepidopteran insects have been cloned from novel lepidopteran-active *B. thuringiensis* microbes. The DNA encoding the *B. thuringiensis* toxins can be used to transform various prokaryotic and eukaryotic microbes to express the *B. thuringiensis* toxins. These recombinant microbes can be used to control lepidopteran insects in various environments.

11 Claims, 1 Drawing Sheet

HD-1    81RR1    81A2    HD-1

BACILLUS THURINGIENSIS ISOLATES ACTIVE AGAINST LEPIDOPTERAN PESTS

CROSS-REFERENCE TO A RELATED APPLICATION

This is a continuation-in-part of co-pending application Ser. No. 353,860, filed May 18, 1989 now abandoned.

BACKGROUND OF THE INVENTION

The most widely used microbial pesticides are derived from the bacterium *Bacillus thuringiensis.* This bacterial agent is used to control a wide range of leaf-eating caterpillars and beetles, as well as mosquitos. *Bacillus thuringiensis* produces a proteinaceous parasporal body or crystal which is toxic upon ingestion by a susceptible insect host. For example, *B. thuringiensis* subsp. kirstaki HD-1 produces a crystal inclusion consisting of a biotoxin called a delta toxin which is toxic to the larvae of a number of lepidopteran insects. The cloning, sequencing, and expression of this B.t. crystal protein gene in *Escherichia coli* has been described in the published literature (Schnepf, H. E. and Whitely, H. R. [1981] Proc. Natl. Acad. Sci. U.S.A. 78:2893-2987; Schnepf et al.). U.S. Pat. No. 4,448,885 and U.S. Pat. No. 4,467,036 both disclose the expression of B.t. crystal protein in *E. coli.*

BRIEF SUMMARY OF THE INVENTION

The subject invention concerns novel *Bacillus thuringiensis* isolates designated B.t. PS81A2 and PS81RR1 which have activity against all lepidopteran pests tested.

Also disclosed and claimed are novel toxin genes which express toxins toxic to lepidopteran insects. These toxin genes can be transferred to suitable hosts via a plasmid vector.

Specifically, the invention comprises novel B.t.. isolates denoted B.t.. PS81A2 and PS81RR1, mutants thereof, and novel delta endotoxin genes derived from these B.t. isolates which encode proteins which are active against lepidopteran pests. More specifically, the gene in B.t. PS81A2 encodes a 133,601 dalton endoxin, whereas the gene in B.t. PS81RR1 encodes a 133,367 dalton endotoxin.

Table 1 discloses the DNA encoding the novel toxin expressed by PS81A2. Table 2 discloses the amino acid sequence of the novel toxin expressed by PS81A2. Table 3 is a composite of Tables 1 and 2. Table 4 discloses the DNA encoding the novel toxin expressed by PS81RR1. Table 5 discloses the amino acid sequence of the novel toxin expressed by PS81RR1. Table 6 is a composite of Tables 4 and 5.

DETAILED DISCLOSURE OF THE INVENTION

Figure 1:
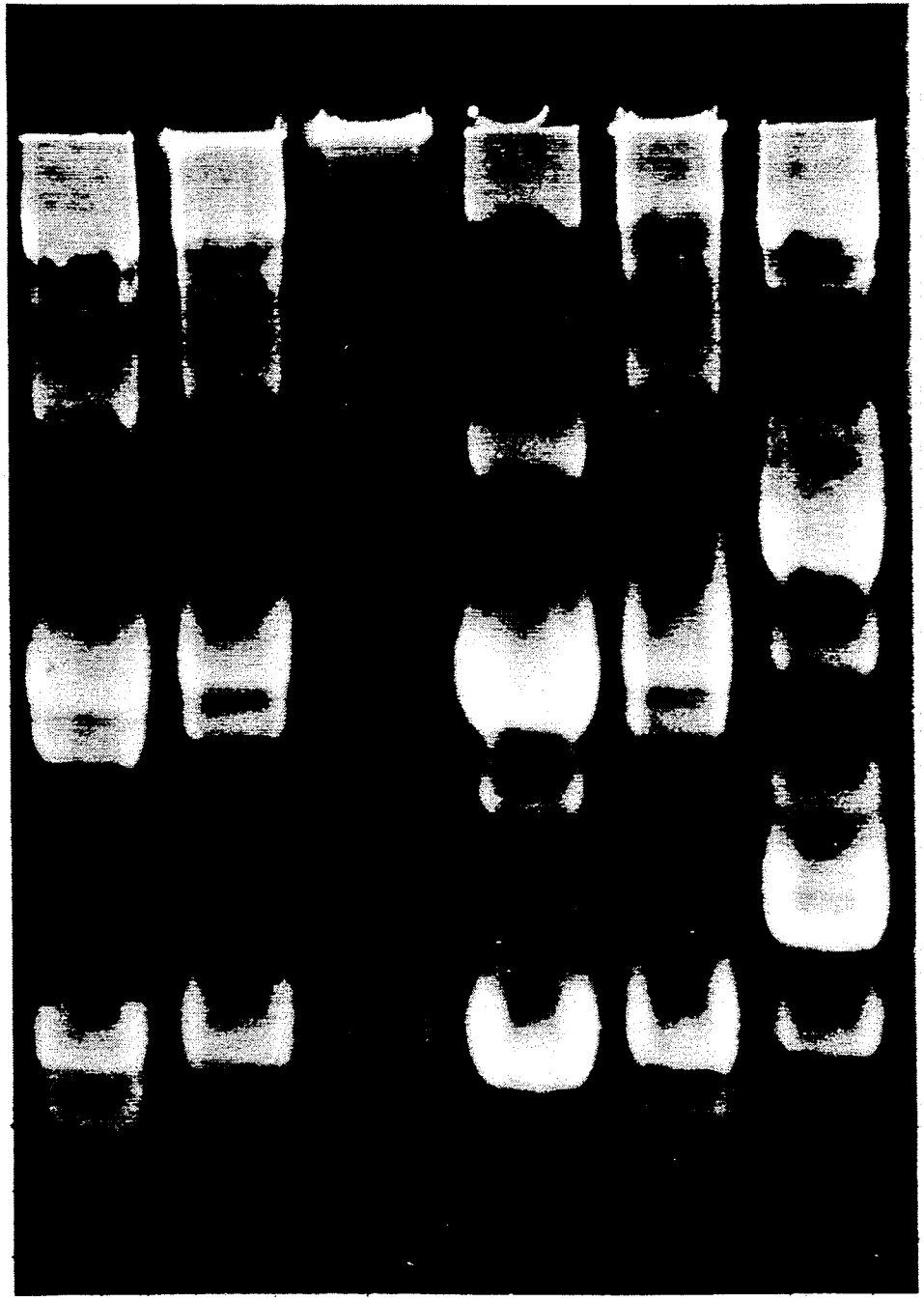
FIG. 1 shows agarose gel electrophoresis of plasmid preparations from B.t. PS81A2, B.t. PS81RR1, and B.t. HD-1.

The novel toxin genes of the subject invention were obtained from novel lepidopteran-active *B. thuringiensis* (B.t.) isolates designated PS81A2 and PS81RR1.

Characteristics of B.t. PS81A2 and PS81RR1

Colony morphology—Large colony, dull surface, typical B.t.

Vegetative cell morphology—typical B.t.

Flagellar serotype—7, aizawai.

Intracellular inclusions—sporulating cells produce a bipyramidal crystal.

Plasmid preparations—agarose gel electrophoresis of plasmid preparations distinguishes B.t. PS81A2 and PS81RR1 from B.t. HD-1 and other B.t. isolates. See FIG. 1.

Alkali-soluble proteins—B.t. PS81A2 and PS81RR1 produce 133,601 and 133,367 dalton proteins, respectively.

Unique toxins—the 133,601 and 133,367 dalton toxins are different from any previously identified.

Activity—B.t. PS81A2 and PS81RR1 both kill all Lepidoptera tested (*Trichoplusia ni, Spodoptera exigua,* and *Plutella xylostella*).

Bioassay procedures:

*Spodoptera exigua*—dilutions are prepared of a spore and crystal pellet, mixed with USDA Insect Diet (Technical Bulletin 1528, U.S. Department of Agriculture) and poured into small plastic trays. Neonate *Spodoptera exigua* larvae are placed on the diet mixture and held at 25° C. Mortality is recorded after six days.

Other insects—dilutions and diet are prepared in the same manner as for the *Spodoptera exigua* bioassay. Fourth instar larvae are used, and mortality is recorded after eight days.

*B. thuringiensis* PS81A2, NRRL B-18457, and *B. thuringiensis* PS81RR1, NRRL B-18458, and mutants thereof, can be cultured using standard known media and fermentation techniques. Upon completion of the fermentation cycle, the bacteria can be harvested by first separating the B.t. spores and crystals from the fermentation broth by means well known in the art. The recovered B.t. spores and crystals can be formulated into a wettable powder, a liquid concentrate, granules or other formulations by the addition of surfactants, dispersants, inert carriers and other components to facilitate handling and application for particular target pests. The formulation and application procedures are all well known in the art and are used with commercial strains of *B. thuringiensis* (HD-1) active against Lepidoptera, e.g., caterpillars. B.t. PS81A2 and B.t. PS81RR1, and mutants thereof, can be used to control lepidopteran pests.

A subculture of B.t. PS81A2 and PS81RR1 and the *E. coli* hosts harboring the toxin genes of the invention, were deposited in the permanent collection of the Northern Research Laboratory, U.S. Department of Agriculture, Peoria, Ill., U.S.A. The accession numbers and deposit dates are as follows:

| Subculture | Accession Number | Deposit Date |
|---|---|---|
| B.t. PS81A2 | NRRL B-18457 | March 14, 1989 |
| B.t. PS81RR1 | NRRL B-18458 | March 14, 1989 |
| *E. coli*(NM522)(pMYC389) | NRRL B-18448 | February 24, 1989 |
| *E. coli*(NM522)(pMYC390) | NRRL B-18449 | February 24, 1989 |

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

The toxin genes of the subject invention can be introduced into a wide variety of microbial hosts. Expression of the toxin gene results, directly or indirectly, in the intracellular production and maintenance of the pesticide. With suitable hosts, e.g., Pseudomonas, the microbes can be applied to the situs of lepidopteran insects where they will proliferate and be ingested by the insects. The result is a control of the unwanted insects. Alternatively, the microbe hosting the toxin gene can be treated under conditions that prolong the activity of the toxin produced in the cell. The treated cell then can be applied to the environment of target pest(s). The resulting product retains the toxicity of the B.t. toxin.

Where the B.t. toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phyloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Bacillus, Pseudomonas, Erwinia, Serratia, Klebsiella, Xanthomonas, Streptomyces, Rhixobium, Rhodopseufomonas, Methylophilius, Agrobacterium, Acetobacter, Lactobaccilus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae. Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii;* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans.* Of particular interest are the pigmented microorganisms.

A wide variety of ways are available for introducing a B.t. gene expressing a toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression would begin. Other techniques may employ a specific nutrient medium in the laboratory, which inhibits the expression of the toxin, where the nutrient medium in the environment would allow for expression of the toxin. For translational initiation, a ribosomal binding site and an initiation codon will be present.

Various manipulations may be employed for enhancing the expression of the messenger RNA, particularly by using an active promoter, as well as by employing sequences, which enhance the stability of the messenger RNA. The transcriptional and translational termination region will involve stop codon(s), a terminator region, and optionally, a polyadenylation signal. A hydrophobic "leader" sequence may be employed at the amino terminus of the translated polypeptide sequence in order to promote secretion of the protein across the inner membrane.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene expressing the toxin. In this manner, the enhanced expression of a siderophore may provide for a competitive advantage for the toxin-producing host, so that it may effectively compete with the wild-type microorganisms and stably occupy a niche in the environment.

Where no functional replication system is present, the construct will also include a sequence of at least 50 basepairs (bp), preferably at least about 100 bp, and usually not more than about 1000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competitive advantage. Therefore, in the event that a toxin gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the Tac promoter, the naturally-occurring promoters associated with the toxin gene, where functional in the host. See for example, U.S. Pat. Nos. 4,332,898, 4,342,832 and 4,356,270. The termination region normally may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSF1010, pRO1614, and the like. See for example, Olson et al., (1982) J. Bacteriol. 150:6069, and Bagdasarian et al., (1981) Gene 16P237, and U.S. Pat. Nos. 4,356,270, 4,362,817, and 4,371,625.

The B.t. gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity.

Suitable host cells, where the pesticide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae, Actinomycetales, and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the B.t. gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and sporobolomyces sp.; phylloplane organisms such as Pseudomonas sp., Erwinia sp. and flavobacterium sp.; or such other organisms as Escherichia, Lactobacillus sp., Bacillus sp., Streptomyces sp., and the like. Specific organisms include *Pseudomonas aeruginose, Pseudomonas fluorescens, Saccharomyces cerevisiae, Bacillus thuringiensis, Escherichia coli, Bacillus subtilis, Streptomyces lividans* and the like.

The cell will usually be intact and be substantially in the proliferative form when treated, rather than in a spore form, although in some instances spores may be employed.

Treatment of the microbial cell, e.g., a microbe containing the B.t. toxin gene, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17-80. More particularly, iodine can be used under milk conditions and for sufficient time to achieve the desired results. Other suitable techniques include treatment with aldehydes, such as formaldehyde and glutaraldehyde; antiinfectives, such as zephiran chloride and cetylpyridinium chloride; alcohols, such as isopropyl and ethanol; various histologic fixatives, such as Lugol iodine, Bouin's fixative, and Helly's fixative (See: Humason, Gretchen L., Animal Tissue Techniques, W. H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

the cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

The cellular host containing the B.t. insecticidal gene may be grown in any convenient nutrient medium, where the DNA construct provides a selective advantage, providing for a selective medium so that substantially all or all of the cells retain the B.t. gene. These cells may then be harvested in accordance with conventional ways. Alternatively, the cells can be treated prior to harvesting.

The B.t. cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The pesticidal concentration will vary widely depending upon the nature of the particular formulation, particularly whether it is a concentrate or to be used directly. The pesticide will be present in at least 1% by weight and may be 100% by weight. The dry formulations will have from about 1-95% by weight of the pesticide while the liquid formulations will generally be from about 1-60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the lepidopteran pest(s), e.g., plants, soil or water, by spraying, dusting, sprinkling, or the like.

Mutants of PS81A2 and PS81RR1 can be made by procedures well known in the art. For example, an asporogenous mutant can be obtained through ethylmethane sulfonate (EMS) mutagenesis of PS81A2 and PS81RR1. The mutants can be made using ultraviolet light and nitrosoguanidine by procedures well known in the art.

A smaller percentage of the asporogenous mutants will remain intact and not lyse for extended fermentation periods; these strains are designated lysis minus (−). Lysis minus strains can be identified by screening asporogenous mutants in shake flask media and selecting those mutants that are still intact and contain toxin crystals at the end of the fermentation. Lysis minus strains are suitable for a cell fixation process that will yield a protected, encapsulated toxin protein.

To prepare a phage resistant variant of said asporogenous mutant, an aliquot of the phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive strain is also plated in the same manner to serve as the positive control. After drying, a drop of the phage lysate is plated in the center of the plate and allowed to dry. Resistant cultures showed no lysis in the area where the phage lysate has been placed after incubation at 30° C. for 24 hours.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing B.t. PS81A2 and PS81RR1

A subculture of B.t. PS81A2 and PS81RR1, or mutants thereof, can be used to inoculate the following medium, a peptone, glucose, salts medium.

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |
| Salts Solution (100 ml) | |
| $MgSO_4.7H_2O$ | 2.46 g |
| $MnSO_4.H_2O$ | 0.04 g |
| $ZnSO_4.7H_2O$ | 0.28 g |
| $FeSO_4.7H_2O$ | 0.40 g |
| $CaCl_2$ Solution (100 ml) | |
| $CaCl_2.2H_2O$ | 3.66 g |
| pH 7.2 | |

The salts solution and CaCl$_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The B.t. spores and/or crystals, obtained in the above fermentation, can be isolated by procedures well known in the art. A frequently-used procedure is to subject the harvested fermentation broth to separation techniques, e.g., centrifugation.

EXAMPLE 2

Cloning of Novel Toxin Gene From Isolate PS81A2 and Transformation into *Escherichia coli*

Total cellular DNA was prepared from B.t. cells grown to a low optical density (OD$_{600}$=1.0). The cells were recovered by centrifugation and protoplasted in TES buffer (30 mM Tris-Cl, 10 mM ethylenediaminetetraacetic acid [EDTA], 50 mM NaCl, pH=8.0) containing 20% sucrose and 50 mg/ml lysozyme. The protoplasts were lysed by addition of sodium dodecyl sulfate (SDS) to a final concentration of 4%. The cellular material was precipitated overnight at 4° C. in 100 mM (final concentration) neutral potassium chloride. The supernate was extracted twice with phenol/chloroform (1:1). The DNA was precipitated with ethanol and purified by isopycnic banding on a cesium gradient.

Total cellular DNA from PS81A2 and B.t.k. HD-1 was digested with EcoRI and separated by electrophoresis on a 0.8% Agarose-TAE-buffered gel. A southern blot of the gel was probed with the NsiI to NsiI fragment of the toxin gene contained in plasmid pM3,130-7 of NRRL B-18332 and the NsiI to KpnI fragment of the "4.5 Kb class" toxin gene (Kronstad and Whitely [1986] Gene U.S.A. 43:29-40). These two fragments were combined and used as the probe. Results show that hybridizing fragments of PS81A2 are distinct from those of HD-1. Specifically, a 3.0 Kb hybridizing band in PS81A2 was detected instead of the 3.8 Kb and 1.8 Kb hybridizing bands seen in HD-1.

Two hundred micrograms of PS81A2 total cellular DNA was digested with EcoRI and separated by electrophoresis on a preparative 0.8% Agarose-TAE gel. The 2.5 Kb to 3.5 Kb region of the gel was cut out and the DNA from it was electroeluted and concentrated using an ELUTIP TM -d (Schleicher and Schuell, Keens, N.H.) ion exchange column. The isolated EcoRI fragments were ligated to LAMBDA ZAP TM EcoRI arms (Stratagene Cloning Systems, La Jolla, Calif.) and packaged using Gigapak GOLD TM (Stratagene) extracts. The packaged recombinant phage were plated with *E. coli* strain BB4 (Stratagene) to give high plaque density. The plaques were screened by standard nucleic acid hybridization procedure with radiolabeled probe. The plaques that hybridized were purified and rescreened at a lower plaque density. The resulting purified phage were grown with R408 M13 helper phage (Stratagene) and the recombinant BlueScript TM (Stratagene) plasmid was automatically excised and packaged. The "phagemid" was re-infected in XL1-Blue *E. coli* cells (Stratagene) as part of the automatic excision process. The infected XL1-Blue cells were screened for ampicillin resistance and the resulting colonies were analyzed by standard miniprep procedure to find the desired plasmid. The plasmid, designated pM6,31-1, contains an approximate 3.0 Kb EcoRI insert and was sequenced using Stratagene's T7 and T3 primers plus a set of existing B.t. endotoxin gene oligonucleotide primers. About 1.8 Kb of the toxin gene was sequenced, and data analysis comparing PS81A2 to other cloned B.t. endotoxin genes showed that the PS81A2 sequence was unique. A synthetic oligonucleotide (CAGATCCACGAGGCTTATCTTCCAGAACTAC) was constructed to one of the regions in the PS81A2 sequence that was least homologous relative to other exiting B.t. endotoxin genes.

PS81A2 total cellular DNA partially digested with Sau3A and fractionated by electrophoresis into a mixture of 9-23 Kb fragments on a 0.6% agarose-TAE gel was ligated into Lambda DASH TM (Stratagene). The packaged phage at a high titer were plated on P2392 *e. coli* cells (Stratagene) and screened using the radiolabeled synthetic oligonucleotide (aforementioned) as a nucleic acid hybridization probe. Hybridizing plaques were rescreened at a lower plaque density. A single purified hybridizing plaque was used to infect P2392 *E. coli* cells in liquid culture for preparation of phage for DNA isolation. DNA was isolated by standard procedures. Preparative amounts of recombinant phage DNA were digested with SalI (to release the inserted DNA from lambda arms) and separated by electrophoresis on a 0.6% Agarose-TAE gel. The large fragments, electroeluted and concentrated as described above, were ligated to SalI-digested and dephosphorylated pUC19 (NEB). The ligation mixture was introduced by transformation into *E. coli* DH5(alpha) competent cells (BRL) and plated on LB agar containing ampicillin, isopropyl-(Beta)-DF-thiogalactoside (IPTG) and 5-Bromo-4-chloro-3-indolyl-(Beta)-D-galactoside (XGAL). White colonies (with insertions in the (Beta)-galactosidase gene of pUC19) were subjected to standard miniprep procedures to isolate the plasmid, designated pM4,122-3. The full length toxin gene was sequenced by using oligonucleotide primers made to the "4.5 Kb class" toxin gene and by "walking" with primers made to the sequence of PS81A2.

The plasmid pM4,122-3 contains about 15 Kb of PS81A2 DNA including the 3.522 Kb which encodes the 133,601 dalton endotoxin. The ORF of the PS81A2 toxin gene was isolated from pM4,122-3 and subcloned into the Bacillus shuttle vector pBClac as a 5.5 Kb blunt-ended DraIII fragment. *E. coli* NM522 cells were transformed and plated on LB agar supplemented with ampicillin. The resulting colonies were analyzed by standard miniprep procedures to isolate plasmids that contained the insert. The desired plasmid, pMYC389, contains the coding sequence of the PS81A2 toxin gene.

EXAMPLE 3

Cloning of Novel Toxin Gene From Isolate PS81RR1 and Transformation in *Escherichia coli*

Total cellular DNA was prepared from B.t. cells grown to a low optical density (OD$_{600}$=1.0). The cells were recovered by centrifugation and protoplasted in TES buffer (30 mM Tris-Cl, 10 mM ethylenediaminetetraacetic acid [EDTA], 50 mM NaCl, pH=8.0) containing 20% sucrose and 50 mg/ml lysozyme. The protoplasts were lysed by addition of sodium dodecyl sulfate (SDS) to a final concentration of 4%. The cellular material was precipitated overnight at 4° C. in 100 mM (final concentration) neutral potassium chloride. The supernate was extracted twice with phenol/chloroform (1:1). The DNA was precipitated with ethanol and purified by isopycnic banding on a cesium chloride gradient.

Total cellular DNA from PS81RR1 and B.t.k. HD-1 was digested with EcoRI and separated by electrophoresis on a 0.8% Agarose-TAE-buffered gel. A southern blot of the gel was probed with the NsiI to NsiI fragment of the toxin gene contained in plasmid pM3,130-7 of NRRL B-18332 and the NsiI to KpnI fragment of the "4.5 Kb class? toxin gene (Kronstad and Whitely [1986] Gene USA 43:29-40). These two fragments were combined and used as the probe. Results show that hybridizing fragments of PS81RR1 are distinct from those of HD-1. specifically, a 2.3 Kb hybridizing band in PS81RR1 was detected instead of the 3.8 Kb and 1.8 Kb hybridizing bands seen in HD-1.

Two hundred micrograms of PS81RR1 total cellular DNA was digested with EcoRI and separated by electrophoresis on a preparative 0.8% Agarose-TAE gel. The 2.2 Kb to 2.4 Kb region of the gel was cut out and the DNA from it was electroeluted and concentrated using an ELUTIP TM-d (Schleicher and Schuell, Keene, N.H.) ion exchange column. The isolated EcoRI fragments were ligated to LAMBDA ZAP TM EcoRI arms (Stratagene Cloning Systems, La Jolla, Calif.) and packaged using Gigapak GOLD TM (Stratagene) extracts. The packaged recombinant phage were plated with E. coli strain BB4 (Stratagene) to give high plaque density. The plaques were screened by standard nucleic acid hybridization procedure with radiolabeled probe. The plaques that hybridized were purified and re-screened at a lower plaque density. The resulting purified phage were grown with R408 M13 helper phage (Stratagene) and the recombinant BlueScript TM (Stratagene) plasmid was automatically excised and packaged. The "phagemid" was re-infected in XL1-Blue E. coli cells (Stratagene) as part of the automatic excision process. The infected XL1-Blue cells were screened for ampicillin resistance and the resulting colonies were analyzed by standard miniprep procedure to find the desired plasmid. The plasmid, designated pM3,31-3, contains an approximate 2.3 Kb EcoRI insert and was sequenced using Stratagene's T7 and T3 primers plus a set of existing B.t. endotoxin oligonucleotide primers. About 600 bp of the toxin gene was sequenced, and data analysis comparing PS81RR1 to other cloned B.t. endotoxin genes showed that the PS81RR1 sequence was unique. A synthetic oligonucleotide (CGTGGATATGGTGAATCTTATC) was constructed to one of the regions in the PS81RR1 sequence that was least homologous relative to other existing B.t. endotoxin genes.

PS81RR1 total cellular DNA partially digested with Sau3A and fractionated by electrophoresis into a mixture of 9-23 Kb fragments on a 0.6% agarose-TAE gel was ligated into Lambda GEM TM-11 ) (PROMEGA). The packaged phage at a high titer were plated on P2392 E. coli cells (Stratagene) and screened using the radiolabeled synthetic oligomnucleotide (aforementioned) as a nucleic acid hybridization probe. Hybridizing plaques were rescreened at a lower plaque density. A single purified hybridizing plaque was used to infect P2392 E. coli cells in liquid culture for preparation of phage for DNA isolation. DNA was isolated by standard procedures. Preparative amounts of recombinant phage DNA were digest with SalI, to release the inserted DNA from lambda arms, and separated by electrophoresis on a 0.6% Agarose-TAE gel. The large fragments, electroeluted and concentrated as described above, were ligated to SalI-digested and dephosphorylated pUC19 (NEB). The ligation mixture was introduced by transformation into E. coli DH5(alpha) competent cells (BRL) and plated on LB agar containing ampicillin, isopropyl-(Beta)-D-thiogalactoside (IPTG) and 5-Bromo-4-Chloro-3-indolyl-(Beta)-D-galactoside (XGAL). White colonies (with insertions in the (Beta)-galactosidase gene of pUC19) were subjected to standard miniprep procedures to isolate the plasmid, designated pM1,RR1-A. The full length toxin gene was sequenced by using oligonucleotide primers made to the "4.5 Kb class" toxin gene and by "walking" with primers made to the sequence of PS81RR1.

The plasmid pM1,RR1-A contains about 13 Kb of PS81RR1 DNA including the 3.540 Kb which encodes the 133,367 dalton endotoxin. The ORF of the PS81RR1 toxin gene was isolated from pM1,RR1-A on a 3.8 Kb NdeI fragment and ligated into the Bacillus shuttle vector pBC1ac. E. coli NM522 cells were transformed and the resulting colonies were analyzed by standard miniprep procedures to isolate plasmids that contained the correct insert. The desired plasmid, pMYC390, contains the coding sequence of the PS81RR1 toxin gene.

The above cloning procedures were conducted using standard procedures unless otherwise noted.

The various methods employed in the preparation of the plasmids and transformation of host organisms are well known in the art. Also, methods for the use of lambda bacteriophage as a cloning vehicle, i.e., the preparation of lambda DNA, in vitro packaging, and transfection of recombinant DNA, are well known in the art. These procedures are all described in Maniatis, T., Fritsch, E. F., and Sambrook, J. (1982) *Molecular Cloning: A Laboratory Manual*, Cold Spring Harbor Laboratory, N.Y. Thus, it is within the skill of those in the genetic engineering art to extract DNA from microbial cells, perform restriction enzyme digestions, electrophorese DNA fragments, tail and anneal plasmid and insert DNA, ligate DNA, transform cells, prepare plasmid DNA, electrophorese proteins, and sequence DNA.

The restriction enzymes disclosed herein can be purchased from Bethesda Research Laboratories, Gaithersburg, MD. New England Biolabs, Beverly, Md. or Boehringer-Mannheim, Indianapolis, Ind. The enzymes are used according to the instructions provided by the supplier.

Plasmid pMYC386 containing the B.t. toxin genes, can be removed from the transformed host microbes by use of standard well-known procedures. For example, E. coli NRRL B-18449 can be subjected to cleared lysate isopycnic density gradient procedures, and the like, to recover pMYC386.

EXAMPLE 4

Insertion of Toxin Genes Into Plants

The novel genes coding for the novel insecticidal toxins, as disclosed herein, can be inserted into plant cells using the Ti plasmid from *Agrobacter tumefaciens*. Plant cells can then be caused to regenerate into plants (Zambryski, P., Joos, H., Gentello, C;, Leemans, J., Van Montague, M. and Schell, J [1983] Cell 32:1033-1043). A particularly useful vector in this regard is pEND4K (Klee, H. J., Yanofsky, M. F. and Nester, E. W. [1985] Bio/Technology 3:637-642). This plasmid can replicate both in plant cells and in bacteria and has multiple cloning sites for passenger genes. The toxin gene, for example, can be inserted into the BamHI site of pEND4K, propagated in *E. coli*, and transformed into appropriate plant cells.

EXAMPLE 5

Cloning of Novel *B. thuringiensis* Genes Into Baculoviruses

The novel genes of the invention can be cloned into baculoviruses such as *Autographa californica* nuclear polyhedrosis virus (AcNPV). Plasmids can be constructed that contain the AcNPV genome cloned into a commercial cloning vector such as pUC8. The AcNPV genome is modified so that the coding region of the polyhedrin gene is removed and a unique cloning site for a passenger gene is placed directly behind the polyhedrin promoter. Examples of such vectors are pGP-B6874, described by Pennock et al. (Pennock, G. D., Shoemaker, C. and Miller, L. K. [1984] Mol. Cell. Biol. 4:399–406), and pAC380, described by Smith et al. (Smith, G. E., Summers, M. D. and Fraser, J. J. [1983] Mol Cell. Biol. 3:2156–2165). The gene coding for the novel protein toxin of the invention can be modified with BamHI linkers at appropriate regions both upstream and downstream from the coding region and inserted into the passenger site of one of the AcNPV vectors.

As disclosed previously, the nucleotide sequences encoding the novel B.t. toxin genes are shown in Tables 1 and 4. The deduced amino acid sequences are shown in Tables 2 and 5.

It is well known in the art that the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| Phenylalanine (Phe) | TTK | Histidine (His) | CAK |
|---|---|---|---|
| Leucine (Leu) | XTY | Glutamine (Gln) | CAJ |
| Isoleucine (Ile) | ATM | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Trp) | TGG |
| Alanine (Ala) | GCL | Arginine (Arg) | WGZ |
| Tyrosine (Tyr) | TAK | Glycine (Gly) | GGL |
| Termination signal | TAJ | | |

Key: Each 3-letter deoxynucleotide triplet corresponds to a trinucleotide of mRNA, having a 5'-end on the left and a 3'-end on the right. All DNA sequences given herein are those of the strand whose sequence correspond to the mRNA sequence, with thymine substituted for uracil. The letters stand for the purine or pyrimidine bases forming the deoxynucleotide sequence.

A = adenine
G = guanine
C = cytosine
T = thymine
X = T or C if Y is A or G
X = C if Y is C or T
Y = A, G, C or T if X is C
Y = A or G if X is T
W = C or A if Z is A or G
W - C if Z is C or T
Z = A, G, C or T if W is C
Z = A or G if W is A
QR = TC if S is A, G, C or T; alternatively QR = AG if S is T or C
J = A or G
K = T or C
L = A, T, C or G
M = A, C or T The above shows that the novel amino acid sequences of the B.t. toxins can be prepared by equivalent nucleotide sequences encoding the same amino acid sequence of the protein. Accordingly, the subject invention includes such equivalent nucleotide sequences. In addition it has been shown that proteins of identified structure and function may be constructed by changing the amino acid sequence if such changes do not alter the protein secondary structure (Kaiser, E. T. and Kezdy, F. J. [1984] Science 223:249–255). Thus, the subject invention includes mutants of the amino acid sequence depicted herein which do not alter the protein secondary structure, or if the structure is altered, the biological activity is retained to some degree.

TABLE 1

| | 10 | 20 | 30 | 40 | 50 | 60 |
|---|---|---|---|---|---|---|
| 1 | ATGGAGAATA | ATATTGAAAA | TCAATGCATA | CCTTACAATT | GTTTAAATAA | TCCTGAAGTA |
| 61 | GAGATATTAG | GGATTGAAAG | GTCAAATAGT | AACGTAGCAG | CAGAAATCGG | CTTGGGGCTT |
| 121 | AGTCGTCTGC | TCGTTTCCCG | AATTCCACTA | GGGGATTTTA | TACTTGGCTT | GTTTGATGTA |
| 181 | ATATGGGGGG | CTATAGGTCC | TTCACAATGG | GATATATTTT | TAGAGCAAAT | TGAGCTATTG |
| 241 | ATCGGCCAAA | GAATAGAGGA | ATTCGCTAGG | AATCAGGCAA | TTTCTAGATT | ACAAGGGCTA |
| | 310 | 320 | 330 | 340 | 350 | 360 |
| 301 | AGCAATCTTT | ACCGAATTTA | CACAAATGCT | TTTAAAAACT | GGGAAGTAGA | TCCTACTAAT |
| 361 | CCAGCATTAA | GAGAAGAGAT | GCGTATTCAA | TTTAATGACA | TGAACAGTGC | TCTTACAACA |
| 421 | GCTATTCCTC | TTTTTTCAGT | TCAAGGTTAT | GAAATTCCTC | TTTTATCAGT | ATATGTTCAA |
| 481 | GCTGCAAATT | TACATTTATC | GGTTTTGAGA | GATGTTTCAG | TGTTTGGACA | ACGTTGGGGA |
| 541 | TTTGATGTAG | CAACAATCAA | TAGTCGTTAT | AATGATTTAA | CTAGGCTTAT | TGGCGAATAT |
| | 610 | 620 | 630 | 640 | 650 | 660 |
| 601 | ACTGATTATG | CTGTACGTTG | GTATAATACG | GGGTTAAATC | GTTTACCACG | TAATGAAGGG |
| 661 | GTACGAGGAT | GGGCAAGATT | TAATAGGTTT | AGAAGAGAGT | TAACAATATC | AGTATTAGAT |
| 721 | ATTATTTCTT | TTTTCCAAAA | TTACGATTCT | AGATTATATC | CAATTCGAC | AATCTATCAA |
| 781 | TTAACGCGGG | AAGTATATAC | AGATCCGGTA | ATTAATATAA | CTGATTATAG | AGTTACCCCA |
| 841 | AGTTTCGAGA | GTATTGAAAA | TTCAGCTATT | AGAAGTCCCC | ATCTTATGGA | TTTCTTAAAT |
| | 910 | 920 | 930 | 940 | 950 | 960 |
| 901 | AATATAATTA | TTGACACTGA | TTTAATTAGA | GGCGTTCACT | ATTGGGCGGG | GCATCGTGTA |
| 961 | ACTTCTCATT | TTACCGGTAG | TTCGCAAGTG | ATAAGCTCCC | CTCAATACGG | GATAACTGCA |
| 1021 | AACGCAGAAC | CGAGTCGAAC | TATTGCTCCT | AGCACTTTTC | CAGGTCTTAA | TCTATTTTAT |
| 1081 | AGAACACTAT | CAGACCCTTT | CTTCCGAAGA | TCCGATAATA | TTATGCCAAC | ATTAGGAATA |
| 1141 | AATGTAGTGC | AGGGGGTAGG | ATTCATTCAA | CCAAATAATG | GTGAAGTTCT | ATATAGAAGG |
| | 1210 | 1220 | 1230 | 1240 | 1250 | 1260 |
| 1201 | AGAGGAACAG | TAGATTCTCT | TGATGAGTTG | CCAATTGACG | GTGAGAATTC | ATTAGTTGGA |

TABLE 1-continued

| | | | | | |
|---|---|---|---|---|---|
| 1261 TATAGTCATA | GATTAAGTCA | CGTTACATTA | ACCAGGTCGT | TATATAATAC | TAATATAACT |
| 1321 AGCTTGCCAA | CATTTGTTTG | GACACATCAC | AGTGCTACTG | ATCGAAATAT | AATCTATCCG |
| 1381 GATGTAATTA | CACAAATACC | ATTGGTAAAA | TCATTCTCCC | TTACTTCAGG | TACCTCTGTA |
| 1441 GTCAGAGGCC | CAGGATTTAC | AGGAGGGGAT | ATCATCCGAA | CTAACGTTAA | TGGTAATGTA |
| | 1510 | 1520 | 1530 | 1540 | 1550 | 1560 |
| 1501 CTAAGTATGA | GTCTTAATTT | TAGTAATACA | TCATTACAGC | GGTATCGCGT | GAGAGTTCGT |
| 1561 TATGCTGCTT | CTCAAACAAT | GGTCATGAGA | GTAAATGTTG | GAGGGAGTAC | TACTTTTGAT |
| 1621 CAAGGATTCC | CTAGTACTAT | GAGTGCAAAT | GGGTCTTTGA | CATCTCAATC | ATTTAGATTT |
| 1681 GCAGAATTTC | CTGTAGGCAT | TAGTACATCT | GGCAGTCAAA | CTGCTGGAAT | AAGTATAAGT |
| 1741 AATAATCCAG | GTAGACAAAC | GTTTCACTTA | GATAGAATTG | AATTTATCCC | AGTTGATGCA |
| | 1810 | 1820 | 1830 | 1840 | 1850 | 1860 |
| 1801 ACATTTGAAG | CAGAATATGA | TTTAGAAAGA | GCACAAAAGG | CGGTGAATTC | GCTGTTTACT |
| 1861 TCTTCCAATC | AAATCGAGTT | AAAAACAGAT | GTGACGGATT | ATCATATTGA | TCAAGTATCC |
| 1921 AATTTAGTAG | ATTGTTTATC | CGATGAATTT | TGTCTGGATG | AAAAGCGAGA | ATTGTCCGAG |
| 1981 AAAGTCAAAC | ATGCGAAGCG | ACTCAGTGAT | GAGCGGAATT | TACTTCAAGA | TCCAAACTTC |
| 2041 AGAGGGATCA | ATAGGCAACC | AGACCGTCCG | TGGAGAGGAA | GTACGGATAT | TACCATCCAA |
| | 2110 | 2120 | 2130 | 2140 | 2150 | 2160 |
| 2101 GGAGGAGATG | ACGTATTCAA | AGAGAATTAC | GTCACACTAC | CAGGTACCTT | TGATGAGTGC |
| 2161 TATCCAACGT | ATTTGTATCA | AAAAATAGAT | GAGTCGAAAT | TAAAAGCCTA | TAACCGTTAC |
| 2221 CAATTAAGAG | GGTATATCGA | AGATAGTCAA | GACTTAGAAA | TCTATTTAAT | TCGCTACAAT |
| 2281 GCAAAACACG | AAACAGTAAA | TGTACCAGGT | ACGGGTTCCT | TATGGCCGCT | TTCAGTCGAA |
| 2341 AGTCCAATTG | GAAGGTGTGG | AGAACCGAAT | CGGTGTGTGC | CACACCTTGA | ATGGAATCCT |
| | 2410 | 2420 | 2430 | 2440 | 2450 | 2460 |
| 2401 GATTTAGATT | GTTCCTGCAG | AGACGGGGAA | AAATGTGCAC | ATCATTCCCA | TCATTTCTCC |
| 2461 TTGGACATTG | ATGTTGGATG | CACAGACTTG | CAAGAGGATC | TAGGCGTGTG | GGTTGTATTC |
| 2521 AAGATTAAGA | CGCAGGAAGG | TTATGCAAGA | TTAGGAAATC | TGGAATTTAT | CGAAGAGAAA |
| 2581 CCATTAATTG | GAGAAGCACT | GTCTCGTGTG | AAGAGAGCGG | AAAAAAAATG | GAGAGACAAA |
| 2641 CGGGAAAAAC | TACAATTGGA | AACAAAACGA | GTATATACAG | AGGCAAAAGA | AGCTGTGGAT |
| | 2710 | 2720 | 2730 | 2740 | 2750 | 2760 |
| 2701 GCTTTATTCG | TAGATTCTCA | ATATGATAGA | TTACAAGCAG | ATACAAACAT | TGGTATGATT |
| 2761 CATGCGGCAG | ATAGACTTGT | TCATCAGATC | CACGAGGCTT | ATCTTCCAGA | ACTACCTTTC |
| 2821 ATTCCAGGAA | TAAATGTGGT | GATTTTTGAA | GAATTAGAAA | ACCGTATTTC | TACTGCATTA |
| 2881 TCCCTATATG | ATGCGAGAAA | TGTCATTAAA | AATGGCGATT | TCAATAATGG | CTTATCATGC |
| 2941 TGGAACGTGA | AAGGGCATGT | AGATGTAGTA | GAACAAAACA | ACCACCGTTC | GGTCCTTGTT |
| | 3010 | 3020 | 3030 | 3040 | 3050 | 3060 |
| 3001 GTCCCGGAAT | GGGAAGCAGA | AGTGTCACAA | ACAATTCGTG | TCTGTCCGGG | GCGTGGCTAT |
| 3061 ATCCTCCGTG | TTACAGCGTA | CAAAGAGGGA | TATGGAGAAG | GTTGCGTAAC | CATCCATGAG |
| 3121 ATCGAGAACA | ATACAGACGA | ACTAAAATTT | AAAAACTGTG | AAGAAGAGGA | AGTGTATCCA |
| 3181 ACGGATACAG | GAACGTGTAA | TAGTTATACT | GCACACCAAG | GTACAGCAGG | ATCCACAGAT |
| 3241 TCATGTAATT | CCCGTAATAT | CAGATATGAG | GATGCATATG | AAATGAATAC | TACAGCATCT |
| | 3310 | 3320 | 3330 | 3340 | 3350 | 3360 |
| 3301 GTTAATTACA | AACCGACTTA | CGAAGAAGAA | AGGTATACAG | ATGTACAAGG | AGATAATCAT |
| 3361 TGTGAATATG | ACAGAGGGTA | TGTGAATTAT | CGACCAGTAC | CAGCTGGTTA | TGTGACAAAA |
| 3421 GAATTAGAGT | ACTTCCCAGA | AACCGATAAG | GTATGGATTG | AGATCGGAGA | AACGGAAGGG |
| 3481 AAGTTTATTG | TAGACAATGT | CGAATTACTC | CTTATGGAGG | AA | |

TABLE 2

| | | | | 5 | | | | | 10 | | | | | 15 |
|---|---|---|---|---|---|---|---|---|---|---|---|---|---|---|
| 1 Met | Glu | Asn | Asn | Ile | Glu | Asn | Gln | Cys | Ile | Pro | Tyr | Asn | Cys | Leu |
| 16 Asn | Asn | Pro | Glu | Val | Glu | Ile | Leu | Gly | Ile | Glu | Arg | Ser | Asn | Ser |
| 31 Asn | Val | Ala | Ala | Glu | Ile | Gly | Leu | Gly | Leu | Ser | Arg | Leu | Leu | Val |
| 46 Ser | Arg | Ile | Pro | Leu | Gly | Asp | Phe | Ile | Leu | Gly | Leu | Phe | Asp | Val |
| 61 Ile | Trp | Gly | Ala | Ile | Gly | Pro | Ser | Gln | Trp | Asp | Ile | Phe | Leu | Glu |
| 76 Gln | Ile | Glu | Leu | Leu | Ile | Gly | Gln | Arg | Ile | Glu | Glu | Phe | Ala | Arg |
| 91 Asn | Gln | Ala | Ile | Ser | Arg | Leu | Gln | Gly | Leu | Ser | Asn | Leu | Tyr | Arg |
| 106 Ile | Tyr | Thr | Asn | Ala | Phe | Lys | Asn | Trp | Val | Asp | Pro | Thr | Asn | Pro |
| 121 Pro | Ala | Leu | Arg | Glu | Glu | Met | Arg | Ile | Gln | Phe | Asn | Asp | Met | Asn |
| 136 Ser | Ala | Leu | Thr | Thr | Ala | Ile | Pro | Leu | Phe | Ser | Val | Gln | Gly | Tyr |
| 151 Glu | Ile | Pro | Leu | Leu | Ser | Val | Tyr | Val | Gln | Ala | Ala | Asn | Leu | His |
| 166 Leu | Ser | Val | Leu | Arg | Asp | Val | Ser | Val | Phe | Gly | Gln | Arg | Trp | Gly |
| 181 Phe | Asp | Val | Ala | Thr | Ile | Asn | Ser | Arg | Tyr | Asn | Asp | Leu | Thr | Arg |
| 196 Leu | Ile | Gly | Glu | Tyr | Thr | Asp | Tyr | Ala | Val | Arg | Trp | Tyr | Asn | Thr |
| 211 Gly | Leu | Asn | Arg | Leu | Pro | Arg | Asn | Glu | Gly | Val | Arg | Gly | Trp | Ala |
| 226 Arg | Phe | Asn | Arg | Phe | Arg | Arg | Glu | Leu | Thr | Ile | Ser | Val | Leu | Asp |
| 241 Ile | Ile | Ser | Phe | Phe | Gln | Asn | Tyr | Asp | Ser | Arg | Leu | Tyr | Pro | Ile |
| 256 Pro | Thr | Ile | Tyr | Gln | Leu | Thr | Arg | Glu | Val | Tyr | Thr | Asp | Pro | Val |
| 271 Ile | Asn | Ile | Thr | Asp | Tyr | Arg | Val | Thr | Pro | Ser | Phe | Glu | Ser | Ile |
| 286 Glu | Asn | Ser | Ala | Ile | Arg | Ser | Pro | His | Leu | Met | Asp | Phe | Leu | Asn |
| 301 Asn | Ile | Ile | Ile | Asp | Thr | Asp | Leu | Ile | Arg | Gly | Val | His | Tyr | Trp |
| 316 Ala | Gly | His | Arg | Val | Thr | Ser | His | Phe | Thr | Gly | Ser | Ser | Gln | Val |
| 331 Ile | Ser | Ser | Pro | Gln | Tyr | Gly | Ile | Thr | Ala | Asn | Ala | Glu | Pro | Ser |
| 346 Arg | Thr | Ile | Ala | Pro | Ser | Thr | Phe | Pro | Gly | Leu | Asn | Leu | Phe | Tyr |
| 361 Arg | Thr | Leu | Ser | Asp | Pro | Phe | Phe | Arg | Arg | Ser | Asp | Asn | Ile | Met |
| 376 Pro | Thr | Leu | Gly | Ile | Asn | Val | Val | Gln | Gly | Val | Gly | Phe | Ile | Gln |
| 391 Pro | Asn | Asn | Gly | Glu | Val | Leu | Tyr | Arg | Arg | Arg | Gly | Thr | Val | Asp |
| 406 Ser | Leu | Asp | Glu | Leu | Pro | Ile | Asp | Gly | Gly | Asn | Ser | Leu | Val | Gly |
| 421 Tyr | Ser | His | Arg | Leu | Ser | His | Val | Thr | Leu | Arg | Ser | Leu | Val | Tyr |
| 436 Asn | Thr | Asn | Ile | Thr | Ser | Leu | Pro | Thr | Phe | Val | Trp | Thr | His | His |
| 451 Ser | Ala | Thr | Asp | Arg | Asn | Ile | Ile | Tyr | Pro | Asp | Val | Ile | Thr | Gln |
| 466 Ile | Pro | Leu | Val | Lys | Ser | Phe | Ser | Leu | Thr | Ser | Gly | Thr | Ser | Val |

TABLE 2-continued

| | | | | | | | | | | | | | | |
|---|---|---|---|---|---|---|---|---|---|---|---|---|---|---|
| 481 | Val | Arg | Gly | Pro | Gly | Phe | Thr | Gly | Gly | Asp | Ile | Ile | Arg | Thr | Asn |
| 496 | Val | Asn | Gly | Asn | Val | Leu | Ser | Met | Ser | Leu | Asn | Phe | Ser | Asn | Thr |
| 511 | Ser | Leu | Gln | Arg | Tyr | Arg | Val | Arg | Val | Arg | Tyr | Ala | Ala | Ser | Gln |
| 526 | Thr | Met | Val | Met | Arg | Val | Asn | Val | Gly | Ser | Gly | Thr | Thr | Phe | Asp |
| 541 | Gln | Gly | Phe | Pro | Ser | Thr | Met | Ser | Ala | Asn | Gly | Ser | Leu | Thr | Ser |
| 556 | Gln | Ser | Phe | Arg | Phe | Ala | Glu | Phe | Pro | Val | Gly | Ile | Ser | Thr | Ser |
| 571 | Gly | Ser | Gln | Thr | Ala | Gly | Ile | Ser | Ile | Ser | Asn | Asn | Pro | Gly | Arg |
| 586 | Gln | Thr | Phe | His | Leu | Asp | Arg | Ile | Glu | Phe | Ile | Pro | Val | Asp | Ala |
| 601 | Thr | Phe | Glu | Ala | Glu | Tyr | Asp | Leu | Glu | Arg | Ala | Gln | Lys | Ala | Val |
| 616 | Asn | Ser | Leu | Phe | Thr | Ser | Ser | Asn | Gln | Ile | Glu | Leu | Lys | Thr | Asp |
| 631 | Val | Thr | Asp | Tyr | His | Ile | Asp | Gln | Val | Ser | Asn | Leu | Val | Asp | Cys |
| 646 | Leu | Ser | Asp | Glu | Phe | Cys | Leu | Asp | Glu | Lys | Arg | Glu | Leu | Ser | Glu |
| 661 | Lys | Val | Lys | His | Ala | Lys | Arg | Leu | Ser | Asp | Glu | Arg | Asn | Leu | Leu |
| 676 | Gln | Asp | Pro | Asn | Phe | Arg | Gly | Ile | Asn | Arg | Gln | Pro | Asp | Arg | Gly |
| 691 | Trp | Arg | Gly | Ser | Thr | Asp | Ile | Thr | Ile | Gln | Gly | Gly | Asp | Asp | Val |
| 706 | Phe | Lys | Glu | Asn | Tyr | Val | Thr | Leu | Pro | Gly | Thr | Phe | Asp | Glu | Cys |
| 721 | Tyr | Pro | Thr | Tyr | Leu | Tyr | Gln | Lys | Ile | Asp | Glu | Ser | Lys | Leu | Lys |
| 736 | Ala | Tyr | Asn | Arg | Tyr | Gln | Leu | Arg | Gly | Tyr | Ile | Glu | Asp | Ser | Gln |
| 751 | Asp | Leu | Glu | Ile | Tyr | Leu | Ile | Arg | Tyr | Asn | Ala | Lys | His | Glu | Thr |
| 766 | Val | Asn | Val | Pro | Gly | Thr | Gly | Ser | Leu | Trp | Pro | Leu | Ser | Val | Glu |
| 781 | Ser | Pro | Ile | Gly | Arg | Cys | Gly | Glu | Pro | Asn | Arg | Cys | Val | Pro | His |
| 796 | Leu | Glu | Trp | Asn | Pro | Asp | Leu | Asp | Cys | Ser | Cys | Arg | Asp | Gly | Glu |
| 811 | Lys | Cys | Ala | His | His | Ser | His | His | Phe | Ser | Leu | Asp | Ile | Asp | Val |
| 826 | Gly | Cys | Thr | Asp | Leu | Gln | Glu | Asp | Leu | Gly | Val | Trp | Val | Val | Phe |
| 841 | Lys | Ile | Lys | Thr | Gln | Glu | Gly | Tyr | Ala | Arg | Leu | Gly | Asn | Leu | Glu |
| 856 | Phe | Ile | Glu | Glu | Lys | Pro | Leu | Ile | Gly | Glu | Ala | Leu | Ser | Arg | Val |
| 871 | Lys | Arg | Ala | Glu | Lys | Lys | Trp | Arg | Asp | Lys | Arg | Glu | Lys | Leu | Gln |
| 886 | Leu | Glu | Thr | Lys | Arg | Val | Tyr | Thr | Glu | Ala | Lys | Glu | Ala | Val | Asp |
| 901 | Ala | Leu | Phe | Val | Asp | Ser | Gln | Tyr | Asp | Arg | Leu | Gln | Ala | Asp | Thr |
| 916 | Asn | Ile | Gly | Met | Ile | His | Ala | Ala | Asp | Arg | Leu | Val | His | Gln | Ile |
| 931 | His | Glu | Ala | Tyr | Leu | Pro | Glu | Leu | Pro | Phe | Ile | Pro | Gly | Ile | Asn |
| 946 | Val | Val | Ile | Phe | Glu | Glu | Leu | Glu | Asn | Arg | Ile | Ser | Thr | Ala | Leu |
| 961 | Ser | Leu | Tyr | Asp | Ala | Arg | Asn | Val | Ile | Lys | Asn | Gly | Asp | Phe | Asn |
| 976 | Asn | Gly | Leu | Ser | Cys | Trp | Asn | Val | Lys | Gly | His | Val | Asp | Val | Val |
| 991 | Glu | Gln | Asn | Asn | His | Arg | Ser | Val | Leu | Val | Val | Pro | Glu | Trp | Glu |
| 1006 | Ala | Glu | Val | Ser | Gln | Thr | Ile | Arg | Val | Cys | Pro | Gly | Arg | Gly | Tyr |
| 1021 | Ile | Leu | Arg | Val | Thr | Ala | Tyr | Lys | Glu | Gly | Tyr | Gly | Glu | Gly | Cys |
| 1036 | Val | Thr | Ile | His | Glu | Ile | Glu | Asn | Asn | Thr | Asp | Glu | Leu | Lys | Phe |
| 1051 | Lys | Asn | Cys | Glu | Glu | Glu | Val | Tyr | Pro | Thr | Asp | Thr | Gly | Thr |
| 1066 | Cys | Asn | Asp | Tyr | Thr | Ala | His | Gln | Gly | Thr | Ala | Gly | Ser | Thr | Asp |
| 1081 | Ser | Cys | Asn | Ser | Arg | Asn | Ile | Arg | Tyr | Glu | Asp | Ala | Tyr | Glu | Met |
| 1096 | Asn | Thr | Thr | Ala | Ser | Val | Asn | Tyr | Lys | Pro | Thr | Tyr | Glu | Glu | Glu |
| 1111 | Arg | Tyr | Thr | Asp | Val | Gln | Gly | Asp | Asn | His | Cys | Glu | Tyr | Asp | Arg |
| 1126 | Gly | Tyr | Val | Asn | Tyr | Arg | Pro | Val | Pro | Ala | Gly | Tyr | Val | Thr | Lys |
| 1141 | Glu | Leu | Glu | Tyr | Phe | Pro | Glu | Thr | Asp | Lys | Val | Trp | Ile | Glu | Ile |
| 1156 | Gly | Glu | Thr | Glu | Gly | Lys | Phe | Ile | Val | Asp | Asn | Val | Glu | Leu | Leu |
| 1171 | Leu | Met | Glu | Glu | | | | | | | | | | | |

TABLE 3

| Pos | AA | Codon | Pos | AA | Codon | Pos | AA | Codon | Pos | AA | Codon | Pos | AA | Codon |
|---|---|---|---|---|---|---|---|---|---|---|---|---|---|---|
| 1 | Met | ATG | 2 | Asn | AAT | 3 | Asn | AAT | 4 | Glu | GAG | 5 | Ile | ATT |
| 6 | Glu | GAA | 7 | Asn | AAT | 8 | Cys | TGC | 9 | Tyr | TAC | 10 | Ile | ATA |
| 11 | Pro | CCT | 12 | Asn | AAT | 13 | Cys | TGT | 14 | Leu | TTA | 15 | Asn | AAT |
| 16 | Pro | CCT | 17 | Glu | GAA | 18 | Val | GTA | 19 | Val | GTA | 20 | Val | GTA |
| 21 | Glu | GAG | 22 | Ile | ATA | 23 | Leu | TTA | 24 | Gly | GGG | 25 | Ile | ATT | 
| 26 | Glu | GAA | 27 | Arg | AGG | 28 | Asn | AAT | 29 | Ala | GCA | 30 | Ser | AGT |
| 31 | Val | GTA | 32 | Asp | GAT | 33 | Ile | ATC | 34 | Asn | AAT | 35 | Glu | GAA |
| 36 | Ala | GCA | 37 | Phe | TTT | 38 | Phe | TTT | 39 | Pro | CCT | 40 | Leu | CTT |
| 41 | Ser | AGT | 42 | Arg | CGT | 43 | Leu | CTG | 44 | Leu | CTC | 45 | Val | GTT | 
| 46 | Leu | CTG | 47 | Arg | CGA | 48 | Pro | CCA | 49 | Gly | GGG | 50 | Ser | AGT |
| 51 | Gly | GGC | 52 | Phe | TTT | 53 | Tyr | TAC | 54 | Asp | GAT | 55 | Leu | CTT |
| 56 | Glu | GAA | 57 | Ile | ATT | 58 | Phe | TTT | 59 | Leu | TTG | 60 | Val | GTA |
| 61 | Ile | ATC | 62 | Trp | TGG | 63 | Gly | GGT | 64 | Gln | CAA | 65 | Leu | CTA |
| 66 | Leu | CTA | 67 | Gln | CAA | 68 | Tyr | TAT | 69 | Leu | CTA | 70 | Trp | TGG |
| 71 | Ala | GCT | 72 | Arg | AGG | 73 | Arg | AGA | 74 | Ser | TCT | 75 | Glu | GAG |
| 76 | Leu | CTT | 77 | Ile | ATT | 78 | Ile | ATT | 79 | Asp | GAT | 80 | Leu | TTG |
| 81 | Ser | AGC | 82 | Asn | AAT | 83 | Ala | GCA | 84 | Arg | CGT | 85 | Ile | ATA | 
| 86 | Ala | GCT | 87 | Asn | AAC | 88 | Thr | ACA | 89 | Gln | CAA | 90 | Glu | GAA |
| 91 | Gly | GGC | 92 | Leu | CTT | 93 | Ile | ATT | 94 | Ala | GCT | 95 | Leu | CTA |
| 96 | Pro | CCA | 97 | Ala | GCA | 98 | Leu | TTA | 99 | Ala | GCA | 100 | Leu | TTG |
| 101 | Ala | GCT | 102 | Asp | GAT | 103 | Val | GTA | 104 | Leu | CTT | 105 | His | CAT |
| 106 | Val | GTT | 107 | Ala | GCA | 108 | Asn | AAC | 109 | Ile | ATT | 110 | Leu | CTA |
| 111 | Ala | GCT | 112 | Ala | GCT | 113 | Ala | GCT | 114 | Trp | TGG | 115 | Ala | GCA |
| 116 | Phe | TTT | 117 | Asp | GAT | 118 | Trp | TGG | 119 | Met | ATG | 120 | Asn | AAT |
| 121 | Gln | CAA | 122 | Val | GTT | 123 | Ser | TCG | 124 | Val | GTT | 125 | Arg | CGA |
| 126 | Met | ATG | 127 | Leu | CTT | 128 | Thr | ACT | 129 | Thr | ACA | 130 | Gln | CAA |
| 131 | Thr | ACT | 132 | Asp | GAT | 133 | Ala | GCT | 134 | Leu | TTA | 135 | Thr | ACA |
| 136 | Val | GTA | 137 | Asn | AAC | 138 | Ala | GCA | 139 | Asn | AAT | 140 | Thr | ACA |
| 141 | Arg | CGA | 142 | Ser | AGT | 143 | Ala | GCA | 144 | Leu | TTA | 145 | Ala | GCA |
| 146 | Ser | TCA | 147 | Val | GTT | 148 | Ile | ATT | 149 | Leu | TTA | 150 | Gln | CAA |
| 151 | Phe | TTT | 152 | Arg | AGA | 153 | Leu | TTA | 154 | Leu | CTT | 155 | Phe | TTT |
| 156 | Arg | CGT | 157 | Tyr | TAT | 158 | Arg | CGT | 159 | Arg | AGA | 160 | Gly | GGA |
| 161 | Trp | TGG | 162 | Tyr | TAT | 163 | Val | GTT | 164 | Leu | TTA | 165 | Arg | AGG |
| 166 | Thr | ACG | 167 | Pro | CCT | 168 | Ser | AGT | 169 | Ile | ATA | 170 | Tyr | TAT |
| 171 | Phe | TTC | 172 | Val | GTA | 173 | Val | GTA | 174 | Thr | ACA | 175 | Leu | TTA |
| 176 | Asn | AAT | 177 | Asn | AAT | 178 | Glu | GAA | 179 | Val | GTT | 180 | Trp | TGG |
| 181 | Ile | ATT | 182 | Leu | CTT | 183 | Pro | CCA | 184 | Ile | ATA | 185 | Pro | CCG |
| 186 | Val | GTA | 187 | Leu | CTT | 188 | Met | ATG | 189 | Phe | TTC | 190 | His | CAT |
| 191 | Ile | ATT | 192 | Ile | ATC | 193 | Arg | AGA | 194 | Pro | CCG | 195 | Val | GTG |
| 196 | Ile | ATT | 197 | Arg | AGA | 198 | Ala | GCT | 199 | Pro | CCC | 200 | Tyr | TAT |
| 201 | Phe | TTC | 202 | Leu | CTT | 203 | Ala | GCG | 204 | Ala | GCA | 205 | Tyr | TAC |
| 206 | Thr | ACC | 207 | Ala | GCA | 208 | Leu | CTT | 209 | Leu | TTA | 210 | Arg | CGT |
| 211 | Arg | CGT | 212 | Leu | TTA | 213 | Ser | TCA | 214 | Thr | ACA | 215 | Gln | CAA |
| 216 | Ala | GCT | 217 | Ile | ATT | 218 | Pro | CCC | 219 | Glu | GAA | 220 | Arg | CGT |
| 221 | Leu | TTA | 222 | Arg | AGA | 223 | Arg | AGA | 224 | Ser | TCA | 225 | Leu | TTA |
| 226 | Thr | ACC | 227 | Val | GTA | 228 | Leu | CTT | 229 | Tyr | TAT | 230 | Thr | ACG |
| 231 | Ser | AGT | 232 | Tyr | TAT | 233 | Leu | TTA | 234 | Asn | AAT | 235 | Leu | TTA |
| 236 | Glu | GAG | 237 | Ser | TCT | 238 | Tyr | TAC | 239 | Glu | GAG | 240 | Pro | CCA |
| 241 | Ala | GCA | 242 | Ala | GCA | 243 | Leu | TTA | 244 | Asn | AAT | 245 | Glu | GAA |
| 246 | Val | GTA | 247 | Phe | TTC | 248 | Tyr | TAT | 249 | Gly | GGC | 250 | Phe | TTT |
| 251 | Ile | ATT | 252 | Ala | GCT | 253 | Ala | GCT | 254 | Pro | CCA | 255 | Thr | ACA |
| 256 | Ile | ATA | 257 | His | CAT | 258 | Arg | AGA | 259 | Pro | CCT | 260 | Asp | GAT |
| 261 | Trp | TGG | 262 | Thr | ACA | 263 | Asn | AAT | 264 | Ile | ATT | 265 | Phe | TTC |
| 266 | Ser | TCT | 267 | Leu | CTT | 268 | Thr | ACA | 269 | Ser | TCA | 270 | Val | GTA |
| 271 | Arg | AGG | 272 | Ile | ATA | 273 | Thr | ACT | 274 | Thr | ACT | 275 | Ile | ATT |
| 276 | Pro | CCC | 277 | Thr | ACA | 278 | Arg | AGA | 279 | Thr | ACA | 280 | Gln | CAA |
| 281 | Ile | ATC | 282 | Val | GTA | 283 | Glu | GAA | 284 | His | CAC | 285 | Tyr | TAT |
| 286 | Phe | TTC | 287 | Glu | GAA | 288 | Val | GTT | 289 | Phe | TTC | 290 | Ile | ATT |
| 291 | Ser | AGT | 292 | Ala | GCA | 293 | Ala | GCT | 294 | Met | ATG | 295 | Ser | TCA |
| 296 | Thr | ACT | 297 | Arg | AGA | 298 | Arg | AGA | 299 | His | CAT | 300 | Asp | GAT |
| 301 | Ala | GCT | 302 | Ala | GCT | 303 | Gly | GGC | 304 | Glu | GAA | 305 | Ile | ATT |
| 306 | Phe | TTC | 307 | Arg | AGA | 308 | Asn | AAT | 309 | Leu | TTA | 310 | Ile | ATT |
| 311 | Ser | AGT | 312 | Ile | ATT | 313 | Pro | CCG | 314 | Ser | TCA | 315 | Leu | CTT |
| 316 | Tyr | TAT | 317 | Ser | AGC | 318 | Val | GTT | 319 | Met | ATG | 320 | Asn | AAT |
| 321 | Asp | GAC | 322 | Phe | TTT | 323 | Gly | GGC | 324 | Gly | GGG | 325 | Asp | GAC |
| 326 | His | CAT | 327 | Ser | TCG | 328 | Ser | TCC | 329 | His | CAT | 330 | Ala | GCG |
| 331 | Arg | AGA | 332 | Ile | ATT | 333 | Arg | AGA | 334 | Gly | GGG | 335 | Gly | GGG |
| 336 | Val | GTA | 337 | Leu | TTA | 338 | Leu | TTA | 339 | Leu | TTA | 340 | Val | GTA |
| 341 | Thr | ACC | 342 | Phe | TTT | 343 | Tyr | TAC | 344 | Ile | ATA | 345 | Pro | CCT |
| 346 | Pro | CCT | 347 | Tyr | TAT | 348 | His | CAT | 349 | Tyr | TAC | 350 | Val | GTG |
| 351 | Thr | ACT | 352 | Pro | CCA | 353 | Ser | TCC | 354 | Pro | CCT | 355 | Gln | CAA |
| 356 | Ile | ATA | 357 | Arg | CGT | 358 | Thr | ACT | 359 | Ala | GCA | 360 | Tyr | — |

TABLE 3-continued

| | | | | | | | | | | | | | | | | | | | |
|---|---|---|---|---|---|---|---|---|---|---|---|---|---|---|---|---|---|---|---|
| AAC | GCA | GAA | CCG | AGT 365 | CGA | ACT | ATT | GCT | CCT 370 | AGC | ACT | TTT | CCA | GGT 375 | AAT | CTA | TTT | TAT 380 | |
| Arg AGA | Thr ACA | Leu CTA | Ser TCA | Asp GAC | Pro CCT | Phe TTC | Phe TTC | Arg CGA | Arg AGA | Ser TCC | Asn AAT | Ile ATT | Gly GGT | Met ATG 395 | Pro CCA | Val GTT | Leu CTA | Gly GGA | Ile ATA 400 |
| Asn AAT | Val GTA | Val GTG | Gln CAG | Gly GGG 385 | Val GTA | Gly GGA | Phe TTC | Ile ATT | Gln CAA 390 | Pro CCA | Asn AAT | Asn AAT | Val GTT | Leu CTA | Leu CTA | Tyr TAT | Arg AGA | Arg AGA 420 | |
| Arg AGA | Gly GGA | Thr ACA | Val GTA | Asp GAT 405 | Ser TCT | Leu CTT | Asp GAT | Glu GAG | Leu TTG 410 | Pro CCA | Ile ATT | Asp GAC | Gly GGT | Glu GAA 415 | Ser TCA | Leu TTA | Val GTT | Gly GGA 440 | |
| Tyr TAT | Ser AGT | His CAT | Arg AGA | Leu TTA 425 | Ser AGT | His CAC | Val GTT | Thr ACA | Leu TTA 430 | Thr ACC | Arg AGG | Ser TCG | Leu TTA | Glu GAG 435 | Thr ACT | Asn AAT | Ile ATA | Thr ACT 460 | |
| Ser AGC | Leu TTG | Pro CCA | Thr ACA | Phe TTT 445 | Val GTT | Trp TGG | Thr ACA | His CAT | His CAC 450 | Ser AGT | Ala GCT | Thr ACT | Asn AAT | Tyr TAT 455 | Ile ATC | Ile ATC | Tyr TAT | Pro CCG 480 | |
| Asp GAT | Val GTA | Ile ATT | Thr ACA | Gln CAA 465 | Ile ATA | Pro CCA | Leu TTG | Val GTA | Lys AAA 470 | Ser TCA | Phe TTC | Arg CGA | Ser TCA | Arg CGA 475 | Thr ACC | Gly GGT | Ser TCT | Val GTA 500 | |
| Val GTA | Arg AGA | Gly GGC | Pro CCA | Gly GGA 485 | Phe TTT | Gly GGA | Ile ATA | Leu CTT | Asp GAT 490 | Ile ATC | Arg CGA | Thr ACT | Val GTT | Thr ACT 495 | Asn AAT | Arg AGA | Ile ATA | Val GTA 520 | |
| Leu CTA | Ser AGT | Met ATG | Ser AGT | Leu CTT 505 | Asn AAT | Phe TTT | Ser AGT | Arg AGG | Thr ACA 510 | Ser TCA | Gln CAG | Val GTT | Arg CGC | Tyr TAT 515 | Val GTG | Thr ACT | Tyr TAT | Arg CGT 540 | |
| Tyr TAT | Ala GCT | Ala GCT | Ser TCT | Gln CAA 525 | Thr ACA | Met ATG | Val GTC | Ala GCT | Arg AGA 530 | Val GTA | Leu TTG | Ser TCT | Ser AGT | Gly GGG 535 | Thr ACT | Phe TTT | Ser TCT | Asp GAT 560 | |
| Gln CAA | Gly GGA | Phe TTC | Pro CCT | Ser AGT 545 | Thr ACT | Met ATG | Ser AGT | Gly GGG | Asn AAT 550 | Gln CAA | Ser TCT | Ser TCC | Gly GGA | Ser TCT 555 | Ser TCA | Phe TTT | Arg AGA | Phe TTT 580 | |
| Ala GCA | Glu GAA | Asn AAT | Pro CCT | Ser AGT 565 | Gly GGC | Ile ATT | Ser AGT | Thr ACA | Ser TCT 570 | Ser AGT | Arg AGA | Ser AGT | Gly GGC | Ala GCT 575 | Ile ATA | Ser AGT | Ile ATA | Ser AGT 600 | |
| Asn AAT | Asn AAT | Val GTA | Pro CCT | Leu CTT 585 | Val GTA | Phe TTT | Leu TTA | His CAC | Leu TTA 590 | Ser TCT | Ser AGT | Arg AGA | Ala GCT | Phe TTT 615 | Pro CCA | Val GTT | Asp GAT | Ala GCA 620 | |
| Thr ACA | Phe TTT | Glu GAA | Ala GCA | Gln CAA 605 | Thr ACA | Met ATG | Lys AAA | Glu GAA | Arg AGA 610 | Leu TTA | Arg AGA | Gln CAG | Gln CAA | Val GTG 635 | Ser TCG | Thr ACT | Phe TTT | Thr ACT 640 | |
| Ser TCT | Ser TCC | Asn AAT | Gln CAA | Glu GAA 625 | Asp GAT | Leu TTA | Asp GAT | Thr ACA | Phe TTT 630 | Ser TCT | Gln CAA | Lys AAG | Thr ACG | His CAT 655 | Asp GAT | Glu GAA | Arg AGA | Ser TCC 660 | |
| Asn AAT | Leu TTA | Val GTA | Asp GAT | Ile ATC 645 | Ser TCC | Met ATG | Lys AAA | Ala GCA | Asp GAT 650 | Phe TTT | Leu TTA | Lys AAG | Leu CTG | Tyr TAT 675 | Glu GAA | Leu TTG | Leu TTG | Glu GAG 680 | |
| Lys AAA | Val GTC | Lys AAA | His CAT | Cys TGT 665 | Arg CGA | Leu TTA | Lys AAA | Gln CAA | Phe TTT 670 | Lys AAA | Lys AAG | Cys TGT | Leu CTT | Leu CTT 695 | Asp GAT | Pro CCA | Phe TTT | Phe TTC 700 | |
| Arg AGA | Gly GGG | Ile ATC | Asn AAT | Ala GCG 685 | Arg AGG | Pro CCA | Asp GAC | Gly GGA | Asp GAT 690 | Arg CGA | Arg AGA | Glu GAG | Ser AGT | Arg CGT 705 | Ile ATT | Thr ACC | Asn AAC | Gln CAA 720 | |
| | | | | Arg AGG 705 | Pro CCA | Asp GAC | Asp GAC | Arg CGT | Gly GGC 710 | Thr ACG 715 | | | | | | | | | |

TABLE 3-continued

| | | | | | | | | | | | | | | | | | |
|---|---|---|---|---|---|---|---|---|---|---|---|---|---|---|---|---|---|
| Gly GGA | Asp GAC | Asp GAC | Val GTA 725 | Phe TTC | Lys AAA | Asn AAT | Tyr TAC 730 | Pro CCA | Leu CTA | Thr ACA | Gly GGT 735 | Thr ACC | Phe TTT | Asp GAT | Glu GAG | Cys TGC 740 | |
| Tyr TAT | Pro CCA | Thr ACG | Tyr TAT | Leu TTG 745 | Tyr TAT | Gln CAA | Asp GAT 750 | Ile ATA | Ser TCG | Lys AAA | Ala GCC | Lys AAA 755 | Ala GCC | Tyr TAT | Asn AAC | Arg CGT | Tyr TAC 760 |
| Gln CAA | Leu TTA | Arg AGA | Tyr TAT | Ile ATC | Tyr TAT | Glu GAA | Gln CAA 770 | Ser AGT | Leu TTA | Glu GAA | Gly GGT | Tyr TAT 775 | Ile ATT | Leu CTT | Arg CGC | Tyr TAC | Asn AAT 780 |
| Ala GCA | Lys AAA | His CAC | Gly GGG | Val GTA | Val GTA | Thr ACA | Val GTA | Pro CCA | Gly GGT | Ser TCC | Val GTG 785 | Ser TCC | Leu CTT | Ser TCA | Trp TGG | Val GTC | Glu GAA |
| Ser AGT | Pro CCA | Ile ATT | Glu GAA | Cys TGT | Gly GGA | Cys TGT | Asn AAT 790 | Pro CCG | Gly GGG | Ala GCA | Asp GAT 795 | Trp TGG | Glu GAA | His CAT | Trp TGG | Asn AAT | Glu GAA 800 |
| Asp GAT | Leu TTA | Asp GAT | Gly GGA | Cys TGC | Arg AGG | Cys TGT | Glu GAA 810 | Pro CCG | Gly GGG | Arg AGA | His CAT 815 | His CAT | Leu CTA | Pro CCA | His CAT | Phe TTC | Pro CCT 820 |
| Leu TTG | Asp GAC | Ile ATT | Cys TGT | Ser TCC | Ile ATT | Arg CGT | Glu GAA 830 | Gly GGG | Asp GAC | Thr ACA | Ala GCA 835 | His CAT | Leu CTA | Ser TCC | Trp TGG | Phe TTC | Ser TCC 840 |
| Lys AAG | Ile ATT | Lys AAG | Asp GAT | Val GTT | Cys TGC | Gly GGT | Leu TTG 850 | Ala GCA | Asn AAT | Ser TCC | Val GTG 855 | Gly GGC | Glu GAA | Ile ATC | His CAT | Val GTA | Phe TTC 860 |
| Pro CCA | Leu TTA | Lys AAA | Thr ACG | Glu GAA | Glu GAA | Arg AGA | Arg AGA 870 | Ala GCA | Thr ACA | Ala GCG | Ala GCA 875 | Glu GAA | Trp TGG | Arg AGA | Val GTG | Glu GAG | Lys AAA 880 |
| Arg CGG | Glu GAA | Phe TTC | Gly GGA | Ala GCA | Ser TCT | Tyr TAT | Leu TTA 890 | Arg CGT | Tyr TAT | Ala GCC | Lys AAA 895 | Lys AAA | Ile ATT | Trp TGG | Ala GCT | Asp GAC | Lys AAA 900 |
| Ala GCT | Leu TTA | Ala GCA | Leu CTA | Val GTA | Gln CAG | Gln CAA | Arg CGA 910 | Lys AAA | Ser TCT | Thr ACA | Thr ACA 915 | Ala GCA | Glu GAA | Gly GGT | Ala GCT | Val GTG | Asp GAT 920 |
| His CAT | Leu CTT | Phe TTC | Val GTA | Ser TCT | Leu CTG | Gln CAA | Arg AGA 930 | Asp GAT | Tyr TAT | Ala GCA | Thr ACA 935 | Leu CTT | Ile ATT | Leu CTA | Gly GGT | Met ATG | Ile ATT 940 |
| Ile ATT | Asn AAC | Ala GCA | Leu CTT | Arg AGA | Gln CAA | Glu GAA | Ile ATC 950 | Gln CAG | His CAT | Ala GCA | Leu CTT 955 | Arg CGT | Ser TCT | Gly GGT | Leu CTA | Pro CCT | Phe TTC 960 |
| Ser TCC | Leu CTA | Tyr TAT | Arg AGA | His CAT | Phe TTT | Asn AAT | Glu GAA 970 | Lys AAA | Glu GAA | Phe TTC | Arg CGT 975 | Asn AAT | Gly GGC | Ser TCG | Thr ACT | Ala GCA | Leu TTA 980 |
| Trp TGG | Asn AAC | Ile ATA | Lys AAA | Ala GCA | Ile ATT | Phe TTT | Ile ATC 990 | Lys AAA | Val GTA | Asn AAT | Ala GCA 995 | Thr ACA | Gly GGG | Ser TCG | Ser TCA | Leu CTT | Cys TGC 1000 |
| Val GTC | Pro CCG | Val GTG | Asp GAT | Val GTA | Ser TCA | Val GTA | Val GTA 1010 | Val GTG | Lys AAA | Ala GCG | His CAC 1015 | Pro CCA | Ile ATT | Gly GGG | Val GTC | Leu CTT | Val GTT 1020 |
| Ile ATC | Leu CTC | Arg CGT | Lys AAA | His CAT | Gly GGA | Tyr TAC | Glu GAG 1030 | Gln CAA | Val GTC | Arg CGT | Cys TGT 1035 | Leu CTT | Gly GGG | Arg CGT | Pro CCT | Gly GGC | Tyr TAT 1040 |
| Ile ATC | Glu GAG | Leu CTC | Thr ACA | Thr ACA | Asn AAT | Phe TTT | Lys AAA 1050 | Glu GAA | Gly GGA | Glu GAA | Cys TGT 1055 | Gln CAA | Thr ACC | Ile ATC | Tyr TAT | His CAT | Glu GAG 1060 |
| Ile ATC | Glu GAG | Thr ACA | Thr ACA | Asp GAC | Asn AAT | Phe TTT | Lys AAA | Pro CCA | Glu GAA | Glu GAA | Glu GAA | Glu GAA | Thr ACC | Glu GAA | Tyr TAT | Tyr TAT | Pro CCA |

TABLE 3-continued

| | | | | 1065 | | | | | 1070 | | | | | 1075 | | | | | 1080 |
|---|---|---|---|---|---|---|---|---|---|---|---|---|---|---|---|---|---|---|---|
| Thr ACG | Asp GAT | Thr ACA | Gly GGA | Thr ACG | Cys TGT | Asn AAT | Asp GAT | Tyr TAT | Thr ACT | Ala GCA | His CAC | Gln CAA | Gly GGT | Thr ACA | Ala GCA | Gly GGA | Ser TCC | Thr ACA | Asp GAT |
| | | | | 1085 | | | | | 1090 | | | | | 1095 | | | | | 1100 |
| Ser TCA | Cys TGT | Asn AAT | Ser TCC | Arg CGT | Asn AAT | Ile ATC | Arg AGA | Tyr TAT | Glu GAG | Asp GAT | Ala GCA | Tyr TAT | Thr ACT | Met ATG | Asn AAT | Thr ACT | Thr ACA | Ala GCA | Ser TCT |
| | | | | 1105 | | | | | 1110 | | | | | 1115 | | | | | 1120 |
| Val GTT | Asn AAT | Tyr TAC | Lys AAA | Pro CCG | Thr ACT | Tyr TAC | Glu GAA | Thr ACA | Glu GAA | Arg AGG | Tyr TAT | Thr ACA | Asp GAT | Val GTA | Gln CAA | Gly GGA | Asp GAT | Val GTG | Ser TCT |
| | | | | 1125 | | | | | 1130 | | | | | 1135 | | | | | 1140 |
| Cys TGT | Glu GAA | Tyr TAT | Asp GAC | Arg AGA | Thr ACT | Gly GGG | Val GTG | Asn AAT | Glu GAA | Arg CGA | Pro CCA | Val GTA | Pro CCA | Ala GCT | Gly GGT | Tyr TAT | Asp GAT | Val GTG | His CAT |
| | | | | 1145 | | | | | 1150 | | | | | 1155 | | | | | 1160 |
| Glu GAA | Leu TTA | Glu GAG | Tyr TAC | Phe TTC | Pro CCA | Trp TGG | Val GTA | Thr ACC | Lys AAG | Val GTA | Ile ATT | Lys AAG | Leu CTC | Ile ATC | Gly GGA | Tyr TAT | Val GTG | Thr ACG | Lys AAA |
| | | | | 1165 | | | | | 1170 | | | | | | | | | | |
| Lys AAG | Phe TTT | Ile ATT | Val GTA | Asp GAC | Asn AAT | Val GTC | Leu TTA | Leu CTC | Glu GAG | Met ATG | Leu CTT | Glu GAG | Glu GAA | Glu GAA | Gly GGG | | | | |

TABLE 4

|  | 10 | 20 | 30 | 40 | 50 | 60 |
|---|---|---|---|---|---|---|
| 1 | ATGGAGATAA | TGAATAATCA | GAATCAATGC | GTTCCTTATA | ACTGTTTGAA | TGATCCGACA |
| 61 | ATTGAAATAT | TAGAAGGAGA | AAGAATGAAA | ACTGGTTACA | CCCCAATAGA | TATTTCCTTG |
| 121 | TCGCTAACGC | AATTTCTGTT | GAGTGAATTT | GTCCCAGGTG | CTGGGTTTGT | ATTAGGTTTA |
| 181 | ATTGATTTAA | TATGGGGGTT | TGTGGGTCCC | TCTCAATGGG | ATGCATTTCT | TGTGCAAATT |
| 241 | GAACAGTTAA | TTAACCAAAG | AATAGAGGAA | TTCGCTAGGA | ACCAAGCAAT | TTCTAGATTA |
|  | 310 | 320 | 330 | 340 | 350 | 360 |
| 301 | GAAGGGCTAA | CCAACCTTTA | TCAAATTTAC | GCAGAAGCTT | TTAGAGAGTG | GGAAGCAGAT |
| 361 | CCTACTAATC | CAGCATTAAC | AGAAGAGATG | CGTATTCAGT | TCAATGACAT | GAACAGTGCT |
| 421 | CTTACAACCG | CTATTCCTCT | TTTTACAGTT | CAAAATTATC | AAGTACCTCT | TCTATCAGTA |
| 481 | TATGTTCAAG | CTGCAAATTT | ACATTTATCG | GTTTTGAGAG | ATGTTTCAGT | GTTTGGACAA |
| 541 | CGTTGGGGAT | TTGATGTAGC | AACAATCGTA | AGTCGTTATA | ATGATTTAAC | TAGGCTTATT |
|  | 610 | 620 | 630 | 640 | 650 | 660 |
| 601 | GGCACCTATA | CAGATTATGC | TGTACGCTGG | TATAATACGG | GATTAGAACG | TGTATGGGGA |
| 661 | CCGGATTCTA | GAGATTGGGT | AAGGTATAAT | CAATTTAGAA | GAGAGCTAAC | ACTAACTGTA |
| 721 | TTAGATATCG | TTTCTCTGTT | CCCGAACTAT | GATAGTAGAA | CGTATCCAAT | TCGAACAGTT |
| 781 | TCCCAATTAA | CTAGAGAAAT | TTATACAAAC | CCAGTATTAG | AAAATTTTGA | TGGTAGTTTT |
| 841 | CGTGGAATGG | CTCAGAGAAT | AGAACAGAAT | ATTAGGCAAC | CACATCTTAT | GGATCCCTT |
|  | 910 | 920 | 930 | 940 | 950 | 960 |
| 901 | AATAGTATAA | CCATTTATAC | TGATGTGCAT | AGAGGCTTTA | ATTATTGGTC | AGGACATCAA |
| 961 | ATAACAGCTT | CTCCTGTCGG | TTTTGCGGGG | CCAGAATTTA | CTTTTCCTAG | ATATGAACC |
| 1021 | ATGGGAAATG | CTGCTCCACC | CGTACTGATC | TCAACTACTG | GTTTGGGGAT | TTTTAGAACA |
| 1081 | TTATCTTCAC | CTCTTTACAG | AAGAATTATA | CTTGGTTCAG | GCCCAAATAA | TCAGAACCTG |
| 1141 | TTTGTCCTTG | ATGGAACGGA | ATTTTCTTTT | GCCTCCCTAA | CAGCCGATTT | ACCTTCTACT |
|  | 1210 | 1220 | 1230 | 1240 | 1250 | 1260 |
| 1201 | ATATACAGAC | AAAGGGGAAC | GGTCGATTCA | CTAGATGTAA | TACCGCCACA | GGATAATAGT |
| 1261 | GTGCCAGCAC | GTGCGGGATT | TAGTCATCGA | TTAAGTCATG | TTACAATGCT | GAGCCAAGCA |
| 1321 | GCTGGAGCAG | TTTACACCTT | GAGAGCTCCA | ACGTTTTCTT | GGCGACATCG | TAGTGCTGAA |
| 1381 | TTCTCTAACC | TAATTCCTTC | ATCACAAATC | ACACAGATAC | CTTTAACAAA | GTCTATTAAT |
| 1441 | CTTGGCTCTG | GGACCTCTGT | TGTTAAGGA | CCAGGATTTA | CAGGAGGAGA | TATTCTTCGA |
|  | 1510 | 1520 | 1530 | 1540 | 1550 | 1560 |
| 1501 | AGAACTTCAC | CTGGCCAGAT | TTCAACCTTA | AGAGTGACTA | TTACTGCACC | ATTATCACAA |
| 1561 | AGATATCGCG | TAAGAATTCG | CTACGCTTCT | ACTACAAATT | TACAATTCCA | TACATCAATT |
| 1621 | GACGGAAGAC | CTATTAATCA | GGGGAATTTT | TCAGCAACTA | TGAGTAGTGG | GGGTAATTTA |
| 1681 | CAGTCCGGAA | GCTTTAGGAC | TGCAGGTTTT | ACTACTCCGT | TTAACTTTTC | AAATGGATCA |
| 1741 | AGTATATTTA | CGTTAAGTGC | TCATGTCTTC | AATTCAGGCA | ATGAAGTTTA | TATAGATCGA |
|  | 1810 | 1820 | 1830 | 1840 | 1850 | 1860 |
| 1801 | ATTGAATTTG | TTCCGGCAGA | AGTAACATTT | GAGGCGGAAT | ATGATTTAGA | AAGAGCGCAA |
| 1861 | GAGGCGGTGA | ATGCTCTGTT | TACTTCTTCC | AATCAACTAG | GATTAAAAAC | AAATGTGACG |
| 1921 | GACTATCATA | TTGATCAAGT | GTCCAATCTA | GTCGAATGTT | TATCCGGTGA | ATTCTGTCTG |
| 1981 | GATGAAAAGA | GAGAATTGTC | CGAGAAAGTC | AAACATGCGA | AGCGACTCAG | TGATGAGCGG |
| 2041 | AATTTACTTC | AAGACCCAAA | CTTCAGAGGC | ATCAATAGAC | AACCAGACCG | TGGCTGGAGA |
|  | 2110 | 2120 | 2130 | 2140 | 2150 | 2160 |
| 2101 | GGCAGTACGG | ATATTACCAT | CCAAGGAGGA | GATGACGTAT | TCAAAGAGAA | TTACGTCACA |
| 2161 | CTACCGGGTA | CCTTTAATGA | GTGTTATCGT | ACGTATCTGT | ATCAAAAAAT | AGATGAGTCG |
| 2221 | AAATTAAAAG | CCTATACCCG | TTACCAATTA | AGAGGGTACA | TCGAGGATAG | TCAAGACTTA |
| 2281 | GAAATCTATT | TAATTCGCTA | CAATACAAAA | CACGAAACAG | TAAATGTGCC | AGGTACGGGT |
| 2341 | TCCTTATGGC | CGCTTTCAGT | CGAAAATCCA | ATTGGAAAGT | GCGGAGAACC | AAATCGATGC |
|  | 2410 | 2420 | 2430 | 2440 | 2450 | 2460 |
| 2401 | GCACCACAAC | TTGAATGGAA | TCCTGATCTA | GATTGTTCCT | GCAGAGACGG | GGAAAAATGT |
| 2461 | GCACATCACT | CCCATCATTT | CTCCTTGGAC | ATTGATATTG | GATGTACAGA | TTTAAATGAG |
| 2521 | AACTTAGGTG | TATGGGTGAT | ATTCAAAATT | AAGACGCAAG | ATGGTCACGC | AAGACTAGGT |
| 2581 | AATCTAGAGT | TTCTCGAAGA | GAAACCATTA | GTAGGCGAAT | CGTTAGCACG | CGTGAAGAGA |
| 2641 | GCGGAGAAGA | AGTGGAGAGA | CAAACGAGAG | AAATTGCAAG | TGGAAACAAA | TATCGTTTAT |
|  | 2710 | 2720 | 2730 | 2740 | 2750 | 2760 |
| 2701 | AAAGAGGCAA | AAGAATCTGT | AGATGCTTTA | TTTGTGAACT | CTCAATATGA | TAGATTACAA |
| 2761 | GCGGATACCG | ACATCGCGAT | CAGAGTTATC | GATTCATGCG | GCAGATAAAC | GCGTTCATCG | 
| 2821 | GCATATCTTC | CAGAGTTATC | TGTAATTCCG | GGTGTCAATG | CGGGCATTTT | TGAAGAATTA |
| 2881 | GAGGGACGTA | TTTTCACAGC | CTACTCTTTA | TATGATGCGA | GAAATGTCAT | TAAAAATGGC |
| 2941 | GATTTCAATA | ATGGCTTATC | ATGCTGGAAC | GTGAAAGGGC | ATGTAGATGT | AGAAGAACAA |
|  | 3010 | 3020 | 3030 | 3040 | 3050 | 3060 |
| 3001 | AACAACCACC | GTTCGGTTCT | TGTTGTCCCG | GAATGGGAAG | CAGAGGTGTC | ACAAGAGGTT |
| 3061 | CGTGTCTGTC | CAGGTCGTGG | CTATATCCTA | CGTGTTACAG | CGTACAAAGA | GGGATATGGA |
| 3121 | GAAGGTTGCG | TAACGATTCA | TGAGATCGAA | GACAATACAG | ACGAACTGAA | ATTCAGCAAC |
| 3181 | TGTGTAGAAG | AGGAAGTATA | TCCAAACAAC | ACGGTAACGT | GTAATGATTA | TACTGCAAAT |
| 3241 | CAAGAAGAAT | ACGGGGTGC | GTACACTTCT | CGTAATCGTG | GATATGGTTA | ATCTTATGAA |
|  | 3310 | 3320 | 3330 | 3340 | 3350 | 3360 |
| 3301 | AGTAATTCTT | CCATACCAGC | TGAGTATGCG | CCAGTTTATG | AGGAAGCATA | TATAGATGGA |
| 3361 | AGAAAGAGA | ATCCTTGTGA | ATCTAACAGA | GGATATGGGG | ATTACACGCC | ACTACCAGCT |
| 3421 | GGTTATGTGA | CAAAAGAATT | AGAGTACTTC | CCAGAAACCG | ATAAGGTATG | GATTGAGATC |
| 3481 | GGGGAAACGG | AAGGAACATT | CATCGTGGAT | AGCGTGGAAT | TACTCCTTAT | GGAGGAA* |

Segment 1-*

TABLE 5

|  |  |  |  | 5 |  |  |  |  | 10 |  |  |  |  | 15 |  |
|---|---|---|---|---|---|---|---|---|---|---|---|---|---|---|---|
| 1 | Met | Glu | Ile | Met | Asn | Asn | Gln | Asn | Gln | Cys | Val | Pro | Tyr | Asn | Cys |
| 16 | Leu | Asn | Asp | Pro | Thr | Ile | Glu | Ile | Leu | Glu | Gly | Glu | Arg | Ile | Glu |
| 31 | Thr | Gly | Tyr | Thr | Pro | Ile | Asp | Ile | Ser | Leu | Ser | Leu | Thr | Gln | Phe |
| 46 | Leu | Leu | Ser | Glu | Phe | Val | Pro | Gly | Ala | Gly | Phe | Val | Leu | Gly | Leu |
| 61 | Ile | Asp | Leu | Ile | Trp | Gly | Phe | Val | Gly | Pro | Ser | Gln | Trp | Asp | Ala |

TABLE 5-continued

| | | | | | | | | | | | | | | | |
|---|---|---|---|---|---|---|---|---|---|---|---|---|---|---|---|
| 76 | Phe | Leu | Val | Gln | Ile | Glu | Gln | Leu | Ile | Asn | Gln | Arg | Ile | Glu | Glu |
| 91 | Phe | Ala | Arg | Asn | Gln | Ala | Ile | Ser | Arg | Leu | Glu | Gly | Leu | Ser | Asn |
| 106 | Leu | Tyr | Gln | Ile | Tyr | Ala | Glu | Ala | Phe | Arg | Glu | Trp | Glu | Ala | Asp |
| 121 | Pro | Thr | Asn | Pro | Ala | Leu | Thr | Glu | Glu | Met | Arg | Ile | Gln | Phe | Asn |
| 136 | Asp | Met | Asn | Ser | Ala | Leu | Thr | Thr | Ala | Ile | Pro | Leu | Phe | Thr | Val |
| 151 | Gln | Asn | Tyr | Gln | Val | Pro | Leu | Leu | Ser | Val | Tyr | Val | Gln | Ala | Ala |
| 166 | Asn | Leu | His | Leu | Ser | Val | Leu | Arg | Asp | Val | Ser | Val | Phe | Gly | Gln |
| 181 | Arg | Trp | Gly | Phe | Asp | Val | Ala | Thr | Ile | Asn | Ser | Arg | Tyr | Asn | Asp |
| 196 | Leu | Thr | Arg | Leu | Ile | Gly | Thr | Tyr | Thr | Asp | Tyr | Ala | Val | Arg | Trp |
| 211 | Tyr | Asn | Thr | Gly | Leu | Glu | Arg | Val | Trp | Gly | Pro | Asp | Ser | Arg | Asp |
| 226 | Trp | Val | Arg | Tyr | Asn | Gln | Phe | Arg | Arg | Glu | Leu | Thr | Leu | Thr | Val |
| 241 | Leu | Asp | Ile | Val | Ser | Leu | Phe | Pro | Asn | Tyr | Asp | Ser | Arg | Thr | Tyr |
| 256 | Pro | Ile | Arg | Thr | Val | Ser | Gln | Leu | Thr | Arg | Glu | Ile | Tyr | Thr | Asn |
| 271 | Pro | Val | Leu | Glu | Asn | Phe | Asp | Gly | Ser | Phe | Arg | Gly | Met | Ala | Gln |
| 286 | Arg | Ile | Glu | Gln | Asn | Ile | Arg | Gln | Pro | His | Leu | Met | Asp | Leu | Leu |
| 301 | Asn | Ser | Ile | Thr | Ile | Tyr | Thr | Asp | Val | His | Arg | Gly | Phe | Asn | Tyr |
| 316 | Trp | Ser | Gly | His | Gln | Ile | Thr | Ala | Ser | Pro | Val | Gly | Phe | Ala | Gly |
| 331 | Pro | Glu | Phe | Thr | Phe | Pro | Arg | Tyr | Gly | Thr | Met | Gly | Asn | Ala | Ala |
| 346 | Pro | Pro | Val | Leu | Ile | Ser | Thr | Thr | Gly | Leu | Gly | Ile | Phe | Arg | Thr |
| 361 | Leu | Ser | Ser | Pro | Leu | Tyr | Arg | Arg | Ile | Ile | Leu | Gly | Ser | Gly | Pro |
| 376 | Asn | Asn | Gln | Asn | Leu | Phe | Val | Leu | Asp | Gly | Thr | Glu | Phe | Ser | Phe |
| 391 | Ala | Ser | Leu | Thr | Ala | Asp | Leu | Pro | Ser | Thr | Ile | Tyr | Arg | Gln | Arg |
| 406 | Gly | Thr | Val | Asp | Ser | Leu | Asp | Val | Ile | Pro | Pro | Gln | Asp | Asn | Ser |
| 421 | Val | Pro | Ala | Arg | Ala | Gly | Phe | Ser | His | Arg | Leu | Ser | His | Val | Thr |
| 436 | Met | Leu | Ser | Gln | Ala | Ala | Gly | Ala | Val | Tyr | Thr | Leu | Arg | Ala | Pro |
| 451 | Thr | Phe | Ser | Trp | Arg | His | Arg | Ser | Ala | Glu | Phe | Ser | Asn | Leu | Ile |
| 466 | Pro | Ser | Ser | Gln | Ile | Thr | Gln | Ile | Pro | Leu | Thr | Lys | Ser | Ile | Asn |
| 481 | Leu | Gly | Ser | Gly | Thr | Ser | Val | Val | Lys | Gly | Pro | Gly | Phe | Thr | Gly |
| 496 | Gly | Asp | Ile | Leu | Arg | Arg | Thr | Ser | Pro | Gly | Gln | Ile | Ser | Thr | Leu |
| 511 | Arg | Val | Thr | Ile | Thr | Ala | Pro | Leu | Ser | Gln | Arg | Tyr | Arg | Val | Arg |
| 526 | Ile | Arg | Tyr | Ala | Ser | Thr | Thr | Asn | Leu | Gln | Phe | His | Thr | Ser | Ile |
| 541 | Asp | Gly | Arg | Pro | Ile | Asn | Gln | Gln | Asn | Phe | Ser | Ala | Thr | Met | Ser |
| 556 | Ser | Gly | Gly | Asn | Leu | Gln | Ser | Gly | Ser | Phe | Arg | Thr | Ala | Thr | Phe |
| 571 | Thr | Thr. | Pro | Phe | Asn | Phe | Ser | Asn | Gly | Ser | Ser | Ile | Phe | Thr | Leu |
| 586 | Ser | Ala | His | Val | Phe | Asn | Ser | Gly | Asn | Glu | Val | Tyr | Ile | Asp | Arg |
| 601 | Ile | Glu | Phe | Val | Pro | Ala | Glu | Val | Thr | Phe | Glu | Ala | Glu | Tyr | Asp |
| 616 | Leu | Glu | Arg | Ala | Gln | Glu | Ala | Val | Asn | Ala | Leu | Phe | Thr | Ser | Ser |
| 631 | Asn | Gln | Leu | Gly | Leu | Lys | Thr | Asn | Val | Thr | Asp | Tyr | His | Ile | Asp |
| 646 | Gln | Val | Ser | Asn | Leu | Val | Glu | Cys | Leu | Ser | Gly | Glu | Phe | Cys | Leu |
| 661 | Asp | Glu | Lys | Arg | Glu | Leu | Ser | Glu | Lys | Val | Lys | His | Ala | Lys | Arg |
| 676 | Leu | Ser | Asp | Glu | Arg | Asn | Leu | Leu | Gln | Asp | Pro | Asn | Phe | Arg | Gly |
| 691 | Ile | Asn | Arg | Gln | Pro | Asp | Arg | Gly | Trp | Arg | Gly | Ser | Thr | Asp | Ile |
| 706 | Thr | Ile | Gln | Gly | Gly | Asp | Asp | Val | Phe | Lys | Glu | Asn | Tyr | Val | Thr |
| 721 | Leu | Pro | Gly | Thr | Phe | Asn | Glu | Cys | Tyr | Pro | Thr | Tyr | Leu | Tyr | Gln |
| 736 | Lys | Ile | Asp | Glu | Ser | Lys | Leu | Lys | Ala | Tyr | Thr | Arg | Tyr | Gln | Leu |
| 751 | Arg | Gly | Tyr | Ile | Glu | Asp | Ser | Gln | Asp | Leu | Glu | Ile | Tyr | Leu | Ile |
| 766 | Arg | Tyr | Asn | Thr | Lys | His | Glu | Thr | Val | Asn | Val | Pro | Gly | Thr | Gly |
| 781 | Ser | Leu | Trp | Pro | Leu | Ser | Val | Glu | Asn | Pro | Ile | Gly | Lys | Cys | Gly |
| 796 | Glu | Pro | Asn | Arg | Cys | Ala | Pro | Gln | Leu | Glu | Trp | Asn | Pro | Asp | Leu |
| 811 | Asp | Cys | Ser | Cys | Arg | Asp | Gly | Glu | Lys | Cys | Ala | His | His | Ser | His |
| 826 | His | Phe | Ser | Leu | Asp | Ile | Asp | Ile | Gly | Cys | Thr | Asp | Leu | Asn | Glu |
| 841 | Asn | Leu | Gly | Val | Trp | Val | Ile | Phe | Lys | Ile | Lys | Thr | Gln | Asp | Gly |
| 856 | His | Ala | Arg | Leu | Gly | Asn | Leu | Glu | Phe | Leu | Glu | Glu | Lys | Pro | Leu |
| 871 | Val | Gly | Glu | Ser | Leu | Ala | Arg | Val | Lys | Arg | Ala | Glu | Lys | Lys | Trp |
| 886 | Arg | Asp | Lys | Arg | Glu | Lys | Leu | Gln | Val | Glu | Thr | Asn | Ile | Val | Tyr |
| 901 | Lys | Glu | Ala | Lys | Glu | Ser | Val | Asp | Ala | Leu | Phe | Val | Asn | Ser | Gln |
| 916 | Tyr | Asp | Arg | Leu | Gln | Ala | Asp | Thr | Asp | Ile | Ala | Met | Ile | His | Ala |
| 931 | Ala | Asp | Lys | Arg | Val | His | Arg | Ile | Arg | Glu | Ala | Tyr | Leu | Pro | Glu |
| 946 | Leu | Ser | Val | Ile | Pro | Gly | Val | Asn | Ala | Gly | Ile | Phe | Glu | Glu | Leu |
| 961 | Glu | Gly | Arg | Ile | Phe | Thr | Ala | Tyr | Ser | Leu | Tyr | Asp | Ala | Arg | Asn |
| 976 | Val | Ile | Lys | Asn | Gly | Asp | Phe | Asn | Asn | Gly | Leu | Ser | Cys | Trp | Asn |
| 991 | Val | Lys | Gly | His | Val | Asp | Val | Glu | Glu | Gln | Asn | Asn | His | Arg | Ser |
| 1006 | Val | Leu | Val | Val | Pro | Glu | Trp | Glu | Ala | Glu | Val | Ser | Gln | Glu | Val |
| 1021 | Arg | Val | Cys | Pro | Gly | Arg | Gly | Tyr | Ile | Leu | Arg | Val | Thr | Ala | Tyr |
| 1036 | Lys | Glu | Gly | Tyr | Gly | Glu | Gly | Cys | Val | Thr | Ile | His | Glu | Ile | Glu |
| 1051 | Asp | Asn | Thr | Asp | Glu | Leu | Lys | Phe | Ser | Asn | Cys | Val | Glu | Glu | Glu |
| 1066 | Val | Tyr | Pro | Asn | Asn | Thr | Val | Thr | Cys | Asn | Asp | Tyr | Thr | Ala | Asn |
| 1081 | Gln | Glu | Glu | Tyr | Gly | Gly | Ala | Tyr | Thr | Ser | Arg | Asn | Arg | Gly | Tyr |
| 1096 | Gly | Glu | Ser | Tyr | Glu | Ser | Asn | Ser | Ser | Ile | Pro | Ala | Glu | Tyr | Ala |
| 1111 | Pro | Val | Tyr | Glu | Glu | Ala | Tyr | Ile | Asp | Gly | Arg | Lys | Glu | Asn | Pro |
| 1126 | Cys | Glu | Ser | Asn | Arg | Gly | Tyr | Gly | Asp | Tyr | Thr | Pro | Leu | Pro | Ala |
| 1141 | Gly | Tyr | Val | Thr | Lys | Glu | Leu | Glu | Tyr | Phe | Pro | Glu | Thr | Asp | Lys |
| 1156 | Val | Trp | Ile | Glu | Ile | Gly | Glu | Thr | Glu | Gly | Thr | PHe | Ile | Val | Asp |
| 1171 | Ser | Val | Glu | Leu | Leu | Leu | Met | Glu | Glu | | | | | | |

Fragment 1-*

TABLE 6

| | | | | 5 | | | | | 10 | | | | | 15 | | | | | 20 |
|---|---|---|---|---|---|---|---|---|---|---|---|---|---|---|---|---|---|---|---|
| Met ATG | Glu GAG | Ile ATA | Met ATG | Asn AAT | Gln CAG | Cys TGC | Gln CAA | Pro CCT | Val GTT | Tyr TAT | Asn AAC | Cys TGT | Leu TTG | Asn AAT | Asp GAT | Pro CCG | Thr ACA |
| | | | | 25 | | | | | 30 | | | | | 35 | | | | | 40 |
| Ile ATT | Glu GAA | Ile ATA | Leu TTA | Asn AAT | Gly GGA | Ile ATA | Glu GAA | Thr ACT | Glu GAA | Tyr TAC | Thr ACC | Pro CCA | Ile ATA | Pro CCA | Asp GAT | Ser TCC | Leu TTG |
| | | | | 45 | | | | | 50 | | | | | 55 | | | | | 60 |
| Ser TCG | Leu CTA | Thr ACG | Gln CAA | Phe TTT | Leu CTG | Leu TTG | Arg AGA | Thr ACT | Phe TTT | Gly GGT | Ala GCT | Pro CCA | Phe TTT | Gly GGG | Val GTA | Ile ATT | Leu TTA |
| | | | | 65 | | | | | 70 | | | | | 75 | | | | | 80 |
| Ile ATT | Asp GAT | Ile ATA | Ile ATT | Trp TGG | Gly GGT | Phe TTT | Arg AGA | Pro CCC | Phe TTT | Trp TGG | Asp GAT | Phe TTT | Ala GCA | Gly GGG | Val GTG | Leu CTT | Ile ATT |
| | | | | 85 | | | | | 90 | | | | | 95 | | | | | 100 |
| Glu GAA | Gln CAG | Ile ATT | Leu TTA | Asn AAT | Gly GGA | Ala GCA | Glu GAA | Pro CCC | Ala GCA | Ala GCT | Asp GAT | Asn AAC | Ala GCA | Glu GAG | Gln CAA | Arg AGA | Ile ATT |
| | | | | 105 | | | | | 110 | | | | | 115 | | | | | 120 |
| Glu GAA | Gly GGG | Ile ATA | Ser AGC | Asn AAC | Leu CTG | Asn AAT | Arg AGA | Tyr TAC | Gln CAA | Arg AGA | Gly GGT | Gln CAG | Ala GCA | Phe TTT | Ala GCT | Arg AGA | Leu TTA |
| | | | | 125 | | | | | 130 | | | | | 135 | | | | | 140 |
| Pro CCT | Thr ACT | Asn AAT | Leu CTT | Ala GCA | Ile ATA | Tyr TAC | Tyr TAT | Arg AGA | Phe TTT | Ala GCA | Phe TTC | Gly GGT | Gln CAA | Asp GAT | Asn AAC | Ala GCA | Asp GAT |
| | | | | 145 | | | | | 150 | | | | | 155 | | | | | 160 |
| Leu CTT | Gln CAG | Thr ACC | Ala GCT | Ile ATT | Leu CTT | Ala GCA | Thr ACA | Met ATG | Val GTT | Gln CAA | Glu GAA | Asn AAT | Val GTA | Asp GAT | Ile ATT | Ser AGT | Ala GCT |
| | | | | 165 | | | | | 170 | | | | | 175 | | | | | 180 |
| Tyr TAT | Val GTT | Phe TTT | Leu TTA | Ala GCA | Leu CTT | His CAT | Phe TTT | Val GTT | Val GTT | Arg AGA | Tyr TAT | Val GTA | ser TCA | Leu TTA | Ile ATA | Ser TCA | Val GTA |
| | | | | 185 | | | | | 190 | | | | | 195 | | | | | 200 |
| Arg CGT | Trp TGG | Thr ACA | Ala GCA | Ala GCA | Ala GCT | Ala GCT | Gln CAA | Arg CGT | Ser TCG | Trp TGG | Tyr TAT | Arg AGA | Val GTT | Asp GAT | Met ATG | Leu CTT | Gln CAA |
| | | | | 205 | | | | | 210 | | | | | 215 | | | | | 220 |
| Gly GGC | Asp GAT | Phe TTT | Thr ACA | Asp GAT | Val GTA | Phe TTC | Ala GCT | Ser AGT | Tyr TAT | Asn AAT | Leu TTA | Leu TTA | Glu GAA | Leu CTT | Arg CGT | Thr ACT | Ile ATT |
| | | | | 225 | | | | | 230 | | | | | 235 | | | | | 240 |
| Pro CCG | Asp GAT | Arg AGA | Thr ACA | Arg AGA | Ala GCT | Ala GCT | Trp TGG | Arg AGA | Asn AAT | Trp TGG | Tyr TAT | Arg AGA | Leu TTA | Glu GAG | Phe TTT | Arg AGG | Thr ACT | Met ATG | Gly GGA |
| | | | | 245 | | | | | 250 | | | | | 255 | | | | | 260 |
| Leu TTA | Met ATG | Leu TTA | Val GTT | Ser TCT | Arg AGA | Gln CAG | Asn AAT | Tyr TAT | Asn AAT | Arg AGA | Leu TTA | Tyr TAT | Glu GAA | Leu TTA | Gln CAA | Thr ACA | Thr ACA | Val GTA |
| | | | | 265 | | | | | 270 | | | | | 275 | | | | | 280 |
| Ser TCC | Asp GAT | Ile ATC | Leu TTA | Arg AGA | Thr ACT | Tyr TAT | Asn AAT | Gln CAA | Asn AAC | Pro CCA | Asn AAT | Tyr TAT | Thr ACG | Glu GAA | Pro CCA | Phe TTT | Thr ACA | Val GTT |
| | | | | 285 | | | | | 290 | | | | | 295 | | | | | 300 |
| Arg CGT | Gln CAG | Ile ATA | Leu TTA | Gln CAG | Val GTG | Asn AAC | Thr ACA | Gln CAG | Arg AGA | Arg AGA | Tyr TAT | Arg AGA | Thr ACA | His CAT | Leu CTC | Trp TGG | Ala GCA |
| | | | | 305 | | | | | 310 | | | | | 315 | | | | | 320 |
| Asn AAT | Ser AGT | Met ATG | Ile ATA | Gln CAG | Asn AAT | Asn AAT | Ala GCG | Val GTG | His CAT | Glu GAA | Pro CCA | Asn AAT | Thr ACA | His CAT | Asp GAT | Met ATG | Ser TCA | Arg AGA | Val GTT |
| | | | | 325 | | | | | 330 | | | | | 335 | | | | | 340 |
| Ile ATA | Thr ACA | Ala GCT | Ile ATA | Ile ATT | | | | Val GTG | His CAT | Ala GCG | Tyr TAT | Thr ACT | Tyr TAT | Ser AGT | Phe TTT | His CAT | Arg AGA | Gln CAA | Leu CTC |
| | | | | 345 | | | | | 350 | | | | | 355 | | | | | 360 |
| Met ATG | Ser TCT | Ala GCT | Asn AAT | Pro CCT | Gly GGT | Gly GGT | Pro CCG | Tyr TAT | Gly GGG | Phe TTT | Phe TTT | His CAT | Gly GGA | Leu TTA | Tyr TAT | Gly GGA | Leu CTT | His CAT | Gly GGA |
| Met | Gly | Asn | Ala | Ala | Pro | Val | Leu | Ser | Ile | Leu | Gly | Tyr | Gly | Ile | Phe | Leu | Gln | Thr ACC | Arg |

TABLE 6-continued

| | | | | | | | | | | | | | | | | | | |
|---|---|---|---|---|---|---|---|---|---|---|---|---|---|---|---|---|---|---|
| ATG | GGA | AAT | GCT | CCA | CCC | GTA | CTG | ATC | TCA | ACT | ACT | GGT | TTG 375 | GGG | ATT | TTT | AGA | ACA 380 |
| Leu TTA | Ser TCT | Ser TCA | Pro CCT | Tyr TAC | Arg AGA | Arg AGA | Ile ATT | Ile ATA 390 | Leu CTT | Gly GGT | Ser TCA | Gly GGT | Pro CCA 395 | Asn AAT | Asn AAT | Gln CAG | Asn AAC | Leu CTG 400 |
| Phe TTT | Val GTC | Leu CTT | Asp GAT | Thr ACG | Glu GAA | Phe TTT | Ser TCT | Phe TTT 410 | Ala GCC | Thr ACA | Leu CTA | Thr ACA | Ala GCC 415 | Asp GAT | Leu TTA | Pro CCT | Ser TCT | Thr ACT 420 |
| Ile ATA | Tyr TAC | Arg AGA | Gln CAA | Gly GGA | Thr ACG | Val GTC | Asp GAT | Ser TCA 430 | Leu CTA | Asp GAT | Val GTA | Ile ATA | Pro CCG 435 | Pro CCA | Gln CAG | Asp GAT | Asn AAT | Ser AGT 440 |
| Val GTG | Pro CCA | Ala GCA | Arg CGT | Gly GGA | Phe TTT | Ser AGT | His CAT | Arg CGA 450 | Leu TTA | Leu TTA | Ser AGT | Val GTT | Met ATG 455 | Met ATG | Leu CTG | Ser AGC | Gln CAA | Ala GCA 460 |
| Ala GCT | Gly GGA | Ala GCA | Val GTT | Tyr TAC | Leu TTG | Arg AGA | Ala GCT | Pro CCA 470 | Thr ACG | His CAT | Ala GCA | Trp TGG | Arg CGA 475 | His CAT | Arg CGT | Pro CCT | Gln CAA | Glu GAA 480 |
| Phe TTC | Ser TCT | Asn AAC | Leu CTA | Pro CCT | Ser TCA | Ser AGT | Gln CAA | Ile ATC 490 | Thr ACA | Ile ATA | Phe TTT | Pro CCT | Leu TTA 495 | Thr ACA | Lys AAG | His CAT | Pro CCA | Asn AAT 500 |
| Leu CTT | Gly GGC | Ser TCT | Gly GGG | Pro CCT | Val GTT | Val GTT | Lys AAA | Gly GGA 510 | Pro CCA | Phe TTT | Thr ACT | Thr ACA | Gly GGA 515 | Gly GGA | Asp GAT | Ser AGC | Leu CTT | Arg CGA 520 |
| Arg AGA | Thr ACT | Arg CGC | Pro CCT | Ser TCT | Ile ATT | Arg CGC | Thr ACC | Leu TTA 530 | Arg AGA | Thr ACA | Asn AAT | Leu TTA | Thr ACT 535 | Ala GCA | Pro CCA | Ser AGT | Ser TCA | Gln CAA 540 |
| Arg AGA | Tyr TAT | Arg CGC | Val GTA | Ala GCA | Arg CGC | Tyr TAC | Ala GCT | Ser TCT 550 | Ile ATT | Met ATG | Leu TTA | Val GTG | Gly GGA 555 | Ala GCA | Phe TTC | His CAT | Ser TCA | Ile ATT 560 |
| Asp GAC | Gly GGA | Arg AGA | Pro CCT | Ser AGT | Gln CAG | Gln CAG | Ala GCT | Phe TTT 570 | Thr ACA | Asn AAT | Met ATG | Phe TTT | Ser AGT 575 | Phe TTC | Ile ATA | Gly GGA | Asn AAT | Leu TTA 580 |
| Gln CAG | Ser TCC | Gly GGA | Ser AGC | Ala GCA | Thr ACT | His CAT | Asn AAT | Phe TTT 590 | Asn AAT | Thr ACT | Asn AAT | Asn AAT | Gln CAA 595 | Phe TTT | Tyr TAT | Val GTT | Thr ACA | Ser TCA 600 |
| Ser AGT | Ile ATA | Phe TTT | Leu TTA | Ser AGT | Ala GCT | Glu GAA | Val GTC | Phe TTC 610 | Thr ACA | Pro CCG | Gly GGC | Phe TTT | Asn AAC 615 | Leu TTA | Glu GAA | Thr ACA | Arg AGA | Arg CGA 620 |
| Ile ATT | Glu GAA | Phe TTT | Phe TTT | Ala GCA | Glu GAA | Phe TTT | Thr ACA | Phe TTT 630 | Gln CAG | Ala GCA | Gly GGC | Tyr TAT | Asp GAT 635 | Glu GAA | Thr ACA | Lys AAG | Asn AAT | Gln CAA 640 |
| Glu GAG | Ala GCG | Val GTG | Asn AAT | Ala GCA | Phe TTT | Val GTG | Ser TCT | Ser TCC 650 | Asn AAT | Glu GAG | Glu GAA | Gly GGA | Leu TTA 655 | Thr ACA | Glu GAA | Thr ACA | Arg AGA | Thr ACG 660 |
| Asp GAC | Tyr TAT | His CAT | Asp GAT | Leu CTG | Val GTG | Ser TCC | Asn AAT | Leu CTA 670 | Val GTC | Cys TGT | Cys TGT | Leu CTA | Ser TCC 675 | Lys AAA | Lys AAA | Gly GGT | Ser AGT | Leu CTG 680 |
| Asp GAT | Glu GAA | Lys AAG | Arg AGA | Gln CAA | Ser TCC | Glu GAG | Lys AAA | Val GTC 690 | Lys AAA | Ala GCG | Ala GCA | Lys AAG | Arg CGA 695 | Gly GGT | Leu CTC | Ser AGT | Cys TGT | Arg CGG 700 |
| Asn AAT | Leu TTA | Leu CTT | Gln CAA | Pro CCA | Asn AAC | Phe TTC | Arg AGA | Gly GGC 710 | Ile ATC | Asn AAT | Asn AAT | Gln CAA | Pro CCA 715 | Asp GAC | Arg CGT | Arg CGT | Trp TGG | Arg AGA 720 |

TABLE 6-continued

| | | | | | | | | | | | |
|---|---|---|---|---|---|---|---|---|---|---|---|
| Gly GGC | Ser AGT | Thr ACG | Asp GAT | Ile ATT 725 | Thr ACC | Gln CAA | Gly GGA | Asp GAT | Val GTA | Phe TTC | Lys AAA 735 | Asn AAT | Tyr TAC | Val GTC | Thr ACA 740 |
| Leu CTA | Pro CCG | Gly GGT | Thr ACC | Phe TTT 745 | Asn AAT | Cys TGT | Tyr TAT | Thr ACG | Pro CCT 750 | Leu CTG | Gln CAA 755 | Ile ATA | Asp GAT | Glu GAG | Ser TCG 760 |
| Lys AAA | Leu TTA | Lys AAA | Ala GCC | Tyr TAT 765 | Thr ACC | Tyr TAC | Gln CAA | Arg AGA | Leu TTA 770 | Ile ATC | Glu GAG 775 | Ser AGT | Gln CAA | Asp GAC | Leu TTA 780 |
| Glu GAA | Ile ATC | Tyr TAT | Leu TTA | Ile ATT 785 | Thr ACC | Tyr TAC | Asn AAT | His CAC | Lys AAA 790 | Pro CCA | Asn AAT 795 | Pro CCA | Gly GGT | Thr ACG | Gly GGT 800 |
| Ser TCC | Leu TTA | Trp TGG | Pro CCG | Trp TGG 805 | Ser TCA | Tyr TAC | Glu GAA | Asp GAT | Leu TTA 810 | Ser TCC | Gly GGA 815 | Gly GGG | Asp GAT | Thr ACG | Cys TGC 820 |
| Ala GCA | Pro CCA | Gln CAA | Leu TTA | Glu GAA 825 | His CAT | Pro CCT | Asp GAT | Arg AGA | Leu CTA 830 | Cys TGC | Arg AGA 835 | Ala GCA | Arg CGC | Thr ACA | Csy TGT 840 |
| Ala GCA | His CAT | Ser TCC | Leu CTT | Ile ATT 785 | Trp TGG | Phe TTC | Cys TGT | Ile ATT | Asp GAC 850 | Gly GGA | Cys TGT 855 | Ser TCG | His CAC | Thr ACA | Glu GAG 860 |
| Asn AAC | Leu TTA | Gly GGT | Val GTA | Trp TGG 865 | His CAT | Lys AAA | Thr ACG | Lys AAG | Ile ATT 870 | Asp GAT | Gly GGT 875 | Ala GCA | Arg CGC | Leu TTA | Gly GGT 880 |
| Asn AAT | Leu CTA | Glu GAG | Phe TTT | Leu CTC 885 | Ala GCG | Ser TCT | Phe TTC | Pro CCA | Leu TTA 890 | Ser TCG | Leu TTA 895 | Ser TCG | Ser TCT | Arg CGC | Arg AGA 900 |
| Ala GCA | Lys AAG | Lys AAA | Thr ACA | Trp TGG 905 | Leu TTA | Trp TGG | Arg CGA | Ala gCT | Glu GAG 910 | Val GTG | Leu TTA 915 | Val GTG | Ile ATC | Arg AGA | Tyr TAT 920 |
| Lys AAA | Ala GCA | Ala GCA | Pro CCA | Glu GAA 925 | Thr ACA | Leu TTA | Val GTA | Lys AAA | Leu TTA 930 | Phe TTT | Gln CAA 935 | Ala GCA | Phe TTT | Ile ATT | Gln CAA 940 |
| Ala GCG | Thr ACC | Thr ACC | Asp GAC | Ile ATC 945 | Ala GCG | His CAT | Met ATG | Asp GAT | Ala GCG 950 | Val GTC | Gly GGC 955 | Gly GGG | Ala GCA | Glu GAA | Glu GAA 960 |
| Ala GCA | Tyr TAT | Leu CTT | Pro CCA | Glu GAG 965 | Leu TTA | Thr ACA | Val GTC | Val GTC | Pro CCG 970 | Val GTC | Asn AAT 975 | Phe TTT | Ile ATT | Asn AAT | Leu TTA 980 |
| Glu GAG | Gly GGA | Arg CGT | Ile ATT | Phe TTC 985 | Ala GCC | Tyr TAC | Asp GAC | Tyr TAT | Leu TTA 990 | Ala GCG | Glu GAA 995 | Ile ATT | Val GTC | Lys AAA | Gly GGC 1000 |
| Asp GAT | Phe TTC | Asn AAT | Lys AAA | Gly GGC 1005 | Ser tCA | Cys TGC | Ser TCT | Trp TGG | Asn AAC 1010 | Val GTA | Val GTA 1015 | Asp GAT | Ser TCA | Glu GAG | Gln CAA 1020 |
| Asp GAT | Asn AAT | Arg CGT | Pro CCA | Ser TCG 1025 | Ala GCG | His CAT | Leu CTT | Lys AAA | Pro CCG 1030 | Phe TTT | Glu GAG 1035 | Arg CGA | Lys AAA | Gln CAA | Val GTT 1040 |
| Asn AAC | Val GTC | Cys TGT | Pro CCA | Gly GGT 1045 | Ala GCG | Val GTT | Lys AAA | Tyr TAT | Leu CTA 1050 | Thr ACA | Tyr TAC 1055 | His CAT | Ser TCA | Gly GGA | Gly GGA |
| Arg CGT | Gly GGT | Cys TGC | Val GTA | Thr ACG | Arg CGT | Ile ATT | Ile ATC | Val GTC | Leu CTA | Thr ACA | Glu GAG 1055 | Ala GCA | Gly GGC | Tyr TAT | Val GTT 1040 |
| Glu GAA | Glu GAA | Cys TGC | Val GTA | Thr ACG | Ile ATT | Ile ATC | Glu GAG | His CAT | Glu GAA 1050 | Thr ACA | Glu GAA | Asp GAC | Lys AAA | Phe TTC | Asn AAC 1060 |

TABLE 6-continued

| Pos | AA | Codon | Pos | AA | Codon | Pos | AA | Codon | Pos | AA | Codon | Pos | AA | Codon |
|---|---|---|---|---|---|---|---|---|---|---|---|---|---|---|
| 1061 | Cys | TGT | 1062 | Val | GTA | 1063 | Glu | GAA | 1064 | Glu | GAG | 1065 | Glu | GAA |
| 1066 | Val | GTA | 1067 | Tyr | TAT | 1068 | Pro | CCA | 1069 | Asn | AAC | 1070 | Asn | AAC |
| 1071 | Thr | ACG | 1072 | Val | GTA | 1073 | Thr | ACG | 1074 | Cys | TGT | 1075 | Asn | AAT |
| 1076 | Asp | GAT | 1077 | Tyr | TAT | 1078 | Thr | ACT | 1079 | Ala | GCA | 1080 | Asn | AAT |
| 1081 | Gln | CAA | 1082 | Glu | GAA | 1083 | Glu | GAA | 1084 | Tyr | TAC | 1085 | Gly | GGG |
| 1086 | Gly | GGT | 1087 | Ala | GCG | 1088 | Tyr | TAC | 1089 | Thr | ACT | 1090 | Ser | TCT |
| 1091 | Arg | CGT | 1092 | Asn | AAT | 1093 | Arg | CGT | 1094 | Gly | GGA | 1095 | Tyr | TAT |
| 1096 | Gly | GGT | 1097 | Glu | GAA | 1098 | Ser | TCT | 1099 | Tyr | TAT | 1100 | Glu | GAA |
| 1101 | Ser | AGT | 1102 | Asn | AAT | 1103 | Ser | TCT | 1104 | Ser | TCC | 1105 | Ile | ATA |
| 1106 | Pro | CCA | 1107 | Ala | GCT | 1108 | Glu | GAG | 1109 | Tyr | TAT | 1110 | Ala | GCG |
| 1111 | Pro | CCA | 1112 | Val | GTT | 1113 | Tyr | TAT | 1114 | Glu | GAG | 1115 | Tyr | TAT |
| 1116 | Ala | GCA | 1117 | Tyr | TAT | 1118 | Ile | ATA | 1119 | Asp | GAT | 1120 | Gly | GGA |
| 1121 | Arg | AGA | 1122 | Lys | AAA | 1123 | Glu | GAG | 1124 | Asn | AAT | 1125 | Pro | CCT |
| 1126 | Cys | TGT | 1127 | Glu | GAA | 1128 | Ser | TCT | 1129 | Asn | AAC | 1130 | Arg | AGA |
| 1131 | Gly | GGA | 1132 | Tyr | TAT | 1133 | Asp | GAT | 1134 | Asp | GAT | 1135 | Glu | GAA |
| 1136 | Tyr | TAC | 1137 | Pro | CCA | 1138 | Leu | CTA | 1139 | Asp | GAT | 1140 | Ala | GCT |
| 1141 | Gly | GGT | 1142 | Tyr | TAT | 1143 | Val | GTG | 1144 | Thr | ACA | 1145 | Lys | AAA |
| 1146 | Glu | GAA | 1147 | Leu | TTA | 1148 | Glu | GAG | 1149 | Tyr | TAC | 1150 | Arg | AGA |
| 1151 | Phe | TTC | 1152 | Glu | GAA | 1153 | Asp | GAT | 1154 | Asp | GAT | 1155 | Tyr | TAC |
| 1156 | Val | GTA | 1157 | Trp | TGG | 1158 | Ile | ATT | 1159 | Pro | CCA | 1160 | Glu | GAG |
| 1161 | Gly | GGG | 1162 | Glu | GAA | 1163 | Thr | ACG | 1164 | Glu | GAA | 1165 | Gly | GGA |
| 1166 | Thr | ACA | 1167 | Phe | TTC | 1168 | Ile | ATC | 1169 | Val | GTG | 1170 | Asp | GAT |
| 1171 | Ser | AGC | 1172 | Val | GTG | 1173 | Leu | TTA | 1174 | Leu | CTC | 1175 | Lys | AAG |
| 1176 | Leu | CTT | 1177 | Met | ATG | 1178 | Glu | GAG | 1179 | Glu | GAA | 1180 | Ile | ATC |

We claim:

1. A process for controlling lepidopteran insect pests which comprises contacting said insect pests with an insect-controlling effective amount of *Bacillus thuringiensis* PS81A2, having all the identifying characteristics of NRRL B-18457, or mutants thereof which have lepidopteran activity.

2. The process, according to claim 1, wherein said mutants are asporogenous mutants and/or phage resistant mutants.

3. The process, according to claim 1, wherein said insect pest is contacted with an insect-controlling effective amount of *Bacillus thuringiensis* PS81A2, by incorporating said *Bacillus thuringiensis* PS81A2 into a bait granule and placing said granule on or in the soil when planting seed of a plant upon which plant insect pest is known to feed.

4. A process for controlling soil-inhabiting insect pests of the order Lepidoptera which comprises
    (1) preparing a bait granule comprising *Bacillus thuringiensis* PS81A2, or mutants thereof, spores or crystals; and
    (2) placing said bait granule on or in the soil.

5. The process, according to claim 4, wherein said bait granule is applied at the same time corn seed is planted in the soil.

6. The process, according to claims 1 or 4, wherein substantially intact *Bacillus thuringiensis* PS81A2 cells, or mutants thereof, which have lepidopteran activity are treated to prolong the pesticidal activity when the substantially intact cells are applied to the environment of a target pest.

7. A composition of matter comprising *Bacillus thuringiensis* PS81A2, or mutants thereof, which have lepidopteran activity spores or crystals in association with an insecticide carrier, wherein said mutants are asporogenous mutants and/or phage resistant mutants.

8. The composition of matter, according to claim 7, wherein said carrier comprises phagostimulants or attractants.

9. A composition of matter comprising *Bacillus thuringiensis* PS81A2, or mutants thereof, which have lepidopteran activity in association with formulation ingredients applied as a seed coating, wherein said mutants are asporogenous mutants and/or phage resistant mutants.

10. *Bacillus thuringiensis* PS81A2 having all the identifying characteristics of NRRL B-18457, or mutants thereof which have lepidopteran activity.

11. Asporogenous and/or phage resistant mutants of *Bacillus thuringiensis* PS81A2.

* * * * *

UNITED STATES PATENT AND TRADEMARK OFFICE
CERTIFICATE OF CORRECTION

PATENT NO.     :  5,164,180

DATED          :  November 17, 1992

INVENTOR(S)    :  Jewel M. Payne and August J. Sick

It is certified that error appears in the above-identified patent and that said Letters Patent is hereby corrected as shown below:

Column 1   line 19:  "kirstaki HD-1" should read --*kurstaki* HD-1--
Column 1   line 25:  "2893-2987" should read --2893-2897--.
Column 3   line 56:  "Rhixobium" should read --*Rhizobium*--.
Column 3   line 57:  "Rhodopseufomonas" should read --*Rhodopseudomonas*--.
Column 5   line 57:  "Gene 16P237" should read --Gene 16:237--.
Column 6   line 57:  "Pseudomonas aeruginose" should read --*Pseudomonas aeruginosa*--.
Column 7   line 5:  "under milk conditions" should read --under mild conditions--.
Column 9   line 48:  "Keens, N.H." should read --Keene, NH--.
Column 10  line 31:  "(Beta)-DF-thiogalactoside" should read --(Beta)-D-thiogalactoside--.
Column 10  line 54:  "Transformation in *Escherichia coli*" should read --Transformation into *Escherichia coli*--.
Column 11  line 7:  "4.5 kb class?" should read --4.5 kb class--.
Column 11  line 46:  "(CGTGGATATGGTGAATCTTATC)" should read --(CGTGGATATGGTGAATCTTATG)--.
Column 11  line 53:  "GEM™-11)(PROMEGA)" should read --GEM™-11 (PROMEGA)--.
Column 11  line 63:  "were digest" should read --were digested--.
Column 12  line 43:  "Beverly, Md" should read --Beverly, MA--.
Column 13  line 19:  "Fraser, J.J." should read --Fraser, M.J.--

UNITED STATES PATENT AND TRADEMARK OFFICE
CERTIFICATE OF CORRECTION

PATENT NO.   : 5,164,180

DATED        : November 17, 1992

INVENTOR(S)  : Jewel M. Payne and August J. Sick

It is certified that error appears in the above-identified patent and that said Letters Patent is hereby corrected as shown below:

Table 1, Nucleotides 2061-2070: "AGACCGTCCG" should read --AGACCGTGGC--.
Table 1, Nucleotides 3201-3210: "TAGTTATACT" should read --TGATTATACT--.
Table 4, Nucleotides 311-320: "CCAACCTTTA" should read --GCAACCTTTA--.

Table 6    Group 51:    "Val    should read --Val
                         TGC"                 GTC--.

Table 6    Group 176:   "ser    should read -- Ser
                         TCA"                  TCA--.

Table 6    Group 236:   "LEu    should read --Leu
                         CTA"                 CTA--.

Table 6    Group 909:   "Ala    should read -- Ala
                         gCT"                  GCT--.

Table 6    Group 972:   "Asp    should read --Asp
                         gAT"                 GAT--.

UNITED STATES PATENT AND TRADEMARK OFFICE
CERTIFICATE OF CORRECTION

PATENT NO. : 5,164,180

DATED : November 17, 1992

INVENTOR(S) : Jewel M. Payne and August J. Sick

It is certified that error appears in the above-identified patent and that said Letters Patent is hereby corrected as shown below:

Table 6    Group 987:    "Ser    should read    -- Ser
                          tCA"                    TCA--.

Signed and Sealed this

Second Day of November, 1993

Attest:

BRUCE LEHMAN

Attesting Officer    Commissioner of Patents and Trademarks